(12) United States Patent
Acharya et al.

(10) Patent No.: US 8,178,355 B2
(45) Date of Patent: May 15, 2012

(54) DETECTION OF VAPOR PHASE COMPOUNDS BY CHANGES IN PHYSICAL PROPERTIES OF A LIQUID CRYSTAL

(75) Inventors: Bharat Acharya, Madison, WI (US); Avijit Sen, Madison, WI (US); Nicholas Abbott, Madison, WI (US); Kurt Kupcho, Madison, WI (US)

(73) Assignee: Platypus Technologies, LLC., Madison, WI (US)

( * ) Notice: Subject to any disclaimer, the term of this patent is extended or adjusted under 35 U.S.C. 154(b) by 0 days.

(21) Appl. No.: 12/560,076

(22) Filed: Sep. 15, 2009

(65) Prior Publication Data

US 2010/0093096 A1 Apr. 15, 2010

Related U.S. Application Data

(60) Provisional application No. 61/096,972, filed on Sep. 15, 2008.

(51) Int. Cl.
*G01N 33/497* (2006.01)
*G01N 21/19* (2006.01)
*G01N 21/41* (2006.01)
*G01N 27/02* (2006.01)
*G01N 27/72* (2006.01)

(52) U.S. Cl. .................. 436/116; 422/82.01; 422/82.02; 422/82.05; 422/82.09; 422/82.11; 422/84; 422/85; 422/86; 422/98; 422/425; 436/100; 436/117; 436/118; 436/120; 436/149; 436/164; 436/166; 436/167; 436/171

(58) Field of Classification Search .................. 73/31.05; 252/299.7; 422/57–58, 82.01–82.02, 82.05, 422/82.09, 82.11, 98, 83–87, 400–401, 408, 422/425; 428/1.6; 436/1, 20, 93, 111–113, 436/116–118, 120–121, 127–128, 130–132, 436/149–150, 164, 166–167, 171, 100
See application file for complete search history.

(56) References Cited

U.S. PATENT DOCUMENTS

| | | | |
|---|---|---|---|
| 3,645,693 A | | 2/1972 | Poziomek et al. |
| 3,910,763 A | | 10/1975 | Poziomek et al. |
| 3,927,977 A | * | 12/1975 | Jacobs ............................ 422/86 |
| 4,068,925 A | | 1/1978 | Tani et al. |
| 4,096,086 A | | 6/1978 | Kanbe et al. |
| 4,285,697 A | | 8/1981 | Neary et al. |
| 4,551,264 A | | 11/1985 | Eidenschink et al. |
| 4,597,942 A | | 7/1986 | Meathrel et al. |

(Continued)

FOREIGN PATENT DOCUMENTS

GB 2297549 7/1996
(Continued)

OTHER PUBLICATIONS

Clements, J. et al, Sensors and Actuators B 1998, 47, 37-42.*

(Continued)

*Primary Examiner* — Arlen Soderquist
(74) *Attorney, Agent, or Firm* — Casimir Jones S.C.

(57) ABSTRACT

The present invention relates to the field of detection of components in gas phase, and in particular to detection of nitric oxide exhaled as a component of breath, using a liquid crystal assay format and a device utilizing liquid crystals as part of a reporting system.

18 Claims, 10 Drawing Sheets

U.S. PATENT DOCUMENTS

| | | | |
|---|---|---|---|
| 4,671,618 A * | 6/1987 | Wu et al. | 349/92 |
| 4,795,253 A | 1/1989 | Sandridge et al. | |
| 4,927,879 A | 5/1990 | Pidgeon | |
| 4,975,249 A * | 12/1990 | Elliott | 422/83 |
| 5,055,408 A | 10/1991 | Higo et al. | |
| 5,059,394 A | 10/1991 | Phillips et al. | |
| 5,063,024 A | 11/1991 | Partanen et al. | |
| 5,073,294 A | 12/1991 | Shannon et al. | |
| 5,132,226 A | 7/1992 | Dreher et al. | |
| 5,141,718 A | 8/1992 | Clark et al. | |
| 5,268,145 A * | 12/1993 | Namba et al. | 422/57 |
| 5,298,394 A | 3/1994 | Arima et al. | |
| 5,368,770 A * | 11/1994 | Saupe et al. | 252/299.01 |
| 5,370,820 A * | 12/1994 | Boden et al. | 252/299.01 |
| 5,370,841 A | 12/1994 | McDonnel et al. | |
| 5,474,796 A | 12/1995 | Brennan | |
| 5,484,565 A | 1/1996 | Larsen et al. | |
| 5,599,919 A | 2/1997 | Yen et al. | |
| 5,601,980 A | 2/1997 | Gordon et al. | |
| 5,700,637 A | 12/1997 | Southern | |
| 5,750,050 A * | 5/1998 | Goodby et al. | 252/299.62 |
| 5,783,445 A * | 7/1998 | Murnick | 436/35 |
| 5,792,860 A * | 8/1998 | McKeown et al. | 540/140 |
| 5,858,659 A | 1/1999 | Sapolsky et al. | |
| 5,908,786 A | 6/1999 | Moreno et al. | |
| 5,925,525 A | 7/1999 | Fodor et al. | |
| 5,942,612 A * | 8/1999 | McKeown et al. | 540/140 |
| 5,985,551 A | 11/1999 | Brennan | |
| 6,001,311 A | 12/1999 | Brennan | |
| 6,017,696 A | 1/2000 | Heller | |
| 6,040,193 A | 3/2000 | Winkler et al. | |
| 6,045,996 A | 4/2000 | Cronin et al. | |
| 6,051,380 A | 4/2000 | Sosnowski et al. | |
| 6,068,818 A | 5/2000 | Ackley et al. | |
| 6,171,780 B1 | 1/2001 | Pham et al. | |
| 6,171,802 B1 | 1/2001 | Wolverton et al. | |
| 6,201,588 B1 | 3/2001 | Walton et al. | |
| 6,242,266 B1 | 6/2001 | Schleifer et al. | |
| 6,277,489 B1 | 8/2001 | Abbott et al. | |
| 6,277,490 B1 | 8/2001 | Ruf | |
| 6,284,197 B1 | 9/2001 | Abbott et al. | |
| 6,288,392 B1 | 9/2001 | Abbott et al. | |
| 6,306,659 B1 | 10/2001 | Parce et al. | |
| 6,423,272 B1 * | 7/2002 | Boden et al. | 422/98 |
| 6,444,254 B1 | 9/2002 | Chilkoti et al. | |
| 6,468,657 B1 | 10/2002 | Hou et al. | |
| 6,586,257 B1 | 7/2003 | Vuong | |
| 6,586,628 B2 | 7/2003 | Abbott | |
| 6,596,545 B1 | 7/2003 | Wagner et al. | |
| 6,692,699 B2 | 2/2004 | Abbott et al. | |
| 6,780,492 B2 | 8/2004 | Abbott | |
| 6,797,463 B2 | 9/2004 | Abbott et al. | |
| 6,824,837 B2 | 11/2004 | Abbott | |
| 6,849,321 B2 | 2/2005 | Abbott et al. | |
| 6,852,285 B2 | 2/2005 | Abbott | |
| 6,858,423 B1 | 2/2005 | Abbott et al. | |
| 6,884,357 B2 | 4/2005 | Siddiqi | |
| 6,963,435 B2 * | 11/2005 | Mallya et al. | 359/238 |
| 7,014,816 B2 * | 3/2006 | Miller et al. | 422/87 |
| 7,018,838 B2 | 3/2006 | Murphy et al. | |
| 7,125,592 B2 | 10/2006 | Abbott | |
| 7,135,143 B2 | 11/2006 | Abbott | |
| 7,303,694 B2 | 12/2007 | Abbott | |
| 7,371,563 B2 | 5/2008 | Duffy et al. | |
| 2002/0004216 A1 | 1/2002 | Abbott et al. | |
| 2002/0028451 A1 | 3/2002 | Abbott et al. | |
| 2002/0052002 A1 | 5/2002 | Niehaus et al. | |
| 2002/0055093 A1 | 5/2002 | Abbott et al. | |
| 2002/0117412 A1 | 8/2002 | Rabiner et al. | |
| 2002/0123134 A1 | 9/2002 | Huang et al. | |
| 2002/0128249 A1 * | 9/2002 | Cook | 514/185 |
| 2002/0142453 A1 | 10/2002 | Abbott et al. | |
| 2002/0164604 A1 | 11/2002 | Abbott et al. | |
| 2002/0172621 A1 | 11/2002 | Barbera-Guillem | |
| 2002/0173033 A1 | 11/2002 | Hammerick et al. | |
| 2003/0032046 A1 | 2/2003 | Duffy et al. | |
| 2003/0049862 A1 | 3/2003 | He et al. | |
| 2003/0071949 A1 | 4/2003 | Abbott | |
| 2003/0099993 A1 | 5/2003 | Abbott et al. | |
| 2003/0124029 A1 | 7/2003 | Webb et al. | |
| 2003/0127396 A1 | 7/2003 | Siddiqi | |
| 2003/0180966 A1 | 9/2003 | Abbott | |
| 2003/0194753 A1 | 10/2003 | Abbott | |
| 2004/0002131 A1 | 1/2004 | Kim et al. | |
| 2004/0009583 A1 | 1/2004 | Benn et al. | |
| 2004/0038408 A1 | 2/2004 | Abbott et al. | |
| 2004/0051838 A1 * | 3/2004 | Inou | 349/187 |
| 2004/0091620 A1 | 5/2004 | Abbott | |
| 2004/0142411 A1 | 7/2004 | Kirk et al. | |
| 2004/0161800 A1 | 8/2004 | Abbott et al. | |
| 2004/0224380 A1 | 11/2004 | Chou et al. | |
| 2005/0064395 A1 | 3/2005 | Israel et al. | |
| 2005/0079486 A1 | 4/2005 | Abbott | |
| 2005/0079487 A1 | 4/2005 | Abbott | |
| 2005/0106562 A1 | 5/2005 | Abbott | |
| 2005/0112544 A1 | 5/2005 | Xu et al. | |
| 2005/0221271 A1 | 10/2005 | Abbott | |
| 2005/0260703 A1 | 11/2005 | Abbott | |
| 2006/0003389 A1 | 1/2006 | Abbott | |
| 2006/0141446 A1 | 6/2006 | Abbott | |
| 2006/0210436 A1 * | 9/2006 | Shenoy | 422/68.1 |
| 2006/0252031 A1 | 11/2006 | Abbott | |
| 2007/0004046 A1 | 1/2007 | Abbott | |
| 2007/0042505 A1 | 2/2007 | Abbott | |
| 2007/0048178 A1 * | 3/2007 | Gu | 422/56 |
| 2007/0099249 A1 | 5/2007 | Abbott | |
| 2007/0099306 A1 * | 5/2007 | Woolverton | 436/518 |
| 2007/0104612 A1 | 5/2007 | Abbott | |
| 2007/0110614 A1 | 5/2007 | Abbott | |
| 2007/0231832 A1 | 10/2007 | Abbott | |
| 2007/0269848 A1 | 11/2007 | Abbott | |
| 2008/0050799 A1 | 2/2008 | Abbott | |
| 2008/0160539 A1 | 7/2008 | Abbott | |
| 2008/0187949 A1 | 8/2008 | Goldbard et al. | |
| 2009/0054262 A1 | 2/2009 | Abbott et al. | |
| 2010/0191474 A1 * | 7/2010 | Haick | 702/19 |

FOREIGN PATENT DOCUMENTS

| | | |
|---|---|---|
| WO | WO 91/18653 A2 | 12/1991 |
| WO | WO 99/63329 | 6/1999 |
| WO | WO 00/50570 A2 | 8/2000 |
| WO | WO 00/73799 | 12/2000 |
| WO | WO 01/61325 A2 | 2/2001 |
| WO | WO 01/61357 A2 | 2/2001 |
| WO | WO 02/071929 A2 | 9/2002 |
| WO | WO 02/075294 | 9/2002 |
| WO | WO 03/019191 | 3/2003 |
| WO | WO 03/021339 A2 | 3/2003 |
| WO | WO 03/029481 | 4/2003 |
| WO | WO 03/081230 | 10/2003 |
| WO | WO 03/086197 | 10/2003 |
| WO | WO 2004/041061 | 5/2004 |
| WO | WO 2004/044583 | 5/2004 |
| WO | WO 2005/010160 | 2/2005 |

OTHER PUBLICATIONS

Winterbottom, D. A. et al, Sensors and Actuators B 2003, 90, 52-57.*
Basova, T. V. et al, Sensors and Actuators B 2003, 96, 70-75.*
Kirchner, N. et al, Chemical Communications 2006, 1512-1514.*
Cadwell, K. D. et al, Sensors and Actuators B 2003, 128, 91-98.*
Wright, J. D. et al, Sensors and Actuators B 1993, 13-14, 276-280.*
Gupta et al, "Optical Amplification of Ligand-Receptor Binding Using Liquid Crystals," Science vol. 279, Mar. 27, 1998 pp. 2077-2080.
Green et al., "Mechanism of the Transformation of a Stiff Polymer Lyotropic Nematic Liquid Crystal to the Cholesteric State by Dopant-Mediated ChiralInformation Transfer", J. Am. Chem. Soc., 1998. 120,9810-9817.
Seung Ryeol Kim et al.. Anal. Chem "A Possible Substrate for Biomolecular Assays Based on Lquid Crystals, Analytical 2 Chemistry,"(2000) 72(19);4646-4653.
Lauer L. et al, "Spot Complaint Neuronal Networks by Structure Optimized Micro-Contact Printing" Biomaterials, Elsevier Science, 2001, vol. 22, pp. 1925-1932.

Kikuchi H E et al, "Culture of Bone-Marrow-Derived Cells in Microfabricated Pit Arrays" Proc SPIE Int Soc Opt Eng; 2001, vol. 4265, pp. 40-49.

Iwuoha E I et al: Reactivities of Organic Phase Biosensors 3: Electrochemical Study of Cytochrome P450 Cam Immobilized in a Methyltriethoysilance Sol-Gel Electroanalysis, VHC Publishers Inc. (2000) vol. 12, p. 980.

Skaife, Justin G et al.. "Quantitative Interpretation of the Optical Textures of Liquid Crystals Caused by Specific Binding of Immunoglobulins to Surface-Bound Antugens," Langmuir (2000) 16(7):3529-3536.

Skaife, Justin G et al, "Quanitative Characterization of Obliquely Deposited Subtrates of Gold by Atomic Force Microscopy: Influence of Subtrate Topography on Anchoring of Liquid Crystals" Chemistry of Materials, V 11(3) 1999, pp. 612-623.

Vinay K. Gupta et al. "Using Droplets of Nematic Liquid Crystal to Probe the Microscopic and Mesoscopic Structure of Organic Surfaces," Langmuir 15:21 (1999) 7213-7223.

R.R. Shah et al.. "Principles for Measurement of Chemical Exposure Based on Recognition-Driven Anchoring Transitions in Liquid Crystals," Science (2001) 393(5533):1296-99.

Kleinfeld D. et al., "Controlled Outgrowth of Dissociated Neurons on Patterned Substrates," J. Neurosci. (1998) 8:4098 120.

Kumar et al.. "Patterned Self-Assembled Monolayers and Meso-Scale Phenomena," Langmuir (1994) 10:1498 511.

Xia Y, "Use of Controlled Reactive Spreading of Liquid Alkanethiol OD the Surface of Gold to Modify the Size of Features Produced by Mierocontact Printing," Whitesides, G., J. Am. Chem. Soc. (1995) 117:327475.

Hickman et al.,"Rational pattern design for in vitro cellular networks using surface photochemistry," J. Vac. Sci. Technol. (1994) 12:607 16.

Jerome, Blandine, "Surface effects and anchoring in liquid crystals," Rep. Prog. Phys. (1991) 54:391 451.

Gupta et al. Design of Surfaces for Patterned Alignment of liquid Crystals on Planar and Curved Substrates, Science (1997) 276:1533-1536.

Drawhorn et al, "Anchoring of Nematic Liquid Crystals on Self-Assembled Monolayers Formed from Alkanethiols on Semitransparent Films of Gold," J. Phys. Chem. (1995) 45:16511.

Ladam, Guy et al, "Protein Adsorption onto Auto-Assembled Polyelectrolyte Films," Langmuir (2001) 17(3):878-882.

Wagner et aL "Covalent Immobilization of Native Biomolecules onto Au(111} via N-Hydroxysuccinimide Ester Functionalized Self-Assembled Monolayers for Scanning Probe Microscopy," Biophys. J. (1996) 70:2052 2066.

Tarlov et al.,"UV Photopatterning of Alkanethiolate Monolayers," J. Am. Chem. Soc (1993) 115: 5305.

Kumar et aL, "Patterned Self-Assembled Monolayers and Meso-Scale Phenomena," Acc. Chem. Res. (1995) 28: 219.

Resler D. P et al, "High-efficiency liquid-crystal optical phased-array beam steering," Opt. Lett. (1996) 21, 689.

Stern, Margaret B, "Binary Optics: A VLSI-based microoptics technology," Microelectron. Eng. (1996) 32. 369.

Goto et aL, "Design of an Aberration-Free Spherical Micro Lens with a Diffractive Relief Grating Film on a Refractive Spherical Glass Substrate," Jpn. J. AppL Phys. (1992) 31,1586.

Magiera et aL,"Hybrid Imaging Element—Possibilities of Aberration Correction," Soc. Photo Opt. Instrum. Eng., (1996) 2774, 204.

Bernard, et al. Affinity capture of proteins from solution and their dissociation by contact printing. Nature Biotechnology. 2001; 19(9):866-869.

Renault et al. "Fabricating Microarrays of Functional Proteins Using Affinity Contact Printing." Angew. Chem. Int. Ed. 2002; 41 (13):2320-2323.

Fast, Cheap, Portable: A New Pathogen Detection Tool. Biomedical Instrumentation & Technology.2002; 36(1):15.

Woolverton, et al. A liquid crystal biosensor for virus detection. Abstracts of the General Meeting of the American Society for Microbiology. 2002;102. (Abstract Only) (1 Pg.).

Espinopza LA, Schumann KR, Luk YY, Israel BA, Abbott NL; Orientational Behavior of Thermotropic Liquid Crystals on Surfaces Presenting Electrostatically Bound Vesicular Stomatitis Virus. Langmuir Mar. 16, 2004; 20(6):2375-85.

Tingey et al. "Imaging of Affinity Microcontact Printed Proteins by Using Liquid Crystals." Langmuir.2004; 20:6816-6826.

Souady, Jamal, et al.; "Structural Profiling of Individual Glycosphingolipids in a Single Thin-Layer Chromatogram by Multiple Sequential Immunodetection Matched with Direct IR-MALDI-o-TOF Mass Spectrometry"; Anal. Chem. (2009); vol. 81, pp. 9481-9492.

* cited by examiner

Figure 1

| LC # | LC Name | Clp./°C | Delta n | Viscosity (20°C) | | Nature |
|---|---|---|---|---|---|---|
| 1 | 5CB | 35 | 0.1918 | 20 | mm²/s | |
| 2 | TL205 | 87 | 0.2175 | 45 | mm²/s | low polarity |
| 3 | E7 | 58 | 0.2253 | 39 | mm²/s | mid polarity |
| 4 | MLC-15700-000 | 95 | 0.2253 | 39 | mm²/s | High Δε |
| 5 | MLC 6812-100 | 69 | 0.0892 | 43 | mm²/s | mid polar |
| 6 | MLC -7800-000 | 100 | 0.0854 | 19 | mm²/s | low polarity |
| 7 | MLC-12200-100 | 66 | 0.1204 | 42 | mm²/s | mid polarity |
| 8 | MLC-6468-000 | | | | | high polar |
| 9 | MLC-9913-1 | 90 | | | | Neg Δε |

Figure 2

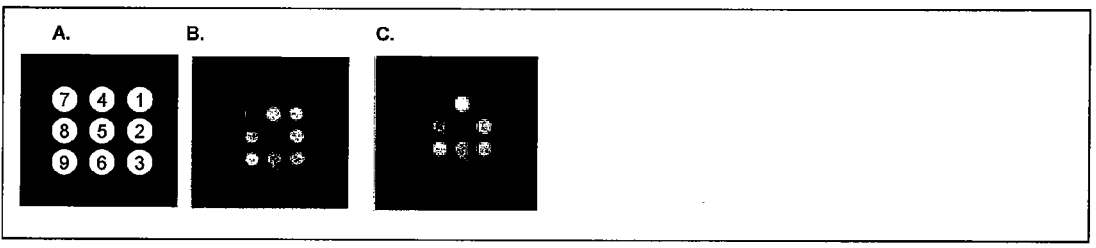

Figure 3

| LC # | LC Name | Clp./°C | Delta n | Viscosity (20°C) | | Nature |
|---|---|---|---|---|---|---|
| 1 | 5CB | 35 | 0.1918 | 20 | mm²/s | |
| 2 | E7 | 58 | 0.2253 | 39 | mm²/s | mid polarity |
| 3 | MLC 6812-100 | 69 | 0.0892 | 43 | mm²/s | mid polar |
| 4 | TL205 | 87 | 0.2175 | 45 | mm²/s | low polarity |
| 5 | MLC-12200-100 | 66 | 0.1204 | 42 | mm²/s | mid polarity |
| 6 | MLC-15700-000 | 95 | 0.2253 | 39 | mm²/s | High Δε |
| 7 | MLC-6468-000 | | | | | high polar |
| 8 | MLC -7800-000 | 100 | 0.0854 | 19 | mm²/s | low polarity |

DETECTION OF VAPOR PHASE COMPOUNDS BY CHANGES IN PHYSICAL PROPERTIES OF A LIQUID CRYSTAL

CROSS REFERENCE TO RELATED APPLICATIONS

This application claims the benefit of U.S. Prov. Appl. No. 61/096,972 filed Sep. 15, 2008, the disclosure of which is incorporated herein by reference in its entirety.

GOVERNMENT SUPPORT

This invention was made in part with government support under DOD contract #W911SR-07-C-0061 and research grant R43ES016389 funded by the NIH/NIEHS. The Government has certain rights in the invention.

FIELD OF THE INVENTION

The present invention relates to the field of detection of different classes of compounds, and in particular to detection of vapor phase compounds using a liquid crystal (LC) assay format and a device utilizing liquid crystals as part of a reporting system.

BACKGROUND OF THE INVENTION

The type and concentration of synthetic chemicals that are in our environment today are of greater concern to government, businesses, and society in general than in any time in history. Multiple factors contribute to this, such as national security concerns related to the use of deadly chemicals as weapons, the risk of an intentional or accidental chemical spill, environmental awareness, and increased concern of the potential impacts of such chemicals on human health. The range of applications for sensors that can accurately measure volatile gases is wide. For example, the Department of Homeland Security needs sensors to detect the presence of chemical weapons, such as chemical warfare agents; and explosives. These sensors can be integrated into traffic lights in large cities, as components of air-intake valves in municipal buildings, and used on-board devices for unmanned aerial vehicles or robotic vehicles that are used to explore hazardous situations. Similar sensors can be used to detect natural gas leaks for home and business owners and to monitor outdoor air in local communities, school playgrounds, or agricultural settings. Industrial manufacturers, on the other hand, need sensors to monitor facility air during production, survey product off-gassing, and assist with maintaining safe levels of permissible exposure limits (PELs) to protect workers against the health effects of exposure to hazardous substances including toxic industrial chemicals. Other industrial applications include monitoring product performance as in the case of interrogating vehicle emissions for release of volatile gases and assessing fruit ripeness based on volatile gas emissions. Another area for application of sensors is in the environmental monitoring for assessment of health effects related to long term exposure to volatile gases such as pesticides and aldehydes and in the arena of food freshness for indicators of spoilage.

There is also broad potential for use of sensors in biomedical applications. For example, sensors have been used to monitor the composition of gas mixtures used for anesthesia during surgical procedures or to monitor the exhaled gases to access the metabolic activities. Recently, analysis of human breath has emerged as a new non-invasive technique for diseases diagnosis. The exhaled human breath contains a number of volatile gases such as oxygen, carbon dioxide, nitrogen, carbon monoxide, acetone, ammonia, hydrogen sulfide, amines, oxides of nitrogen etc. (Manolis, 1983; Smith et al, 1999; and Diskin et al, 2003). Measurements of analytes in exhaled breath can be applied to a wide range of disease states, including diabetes (Henderson et al, 1952; Sulway et al, 1970; Crofford et al, 1977; and Novak et al, 2007) and gastrointestinal disorders (Perman, 1991; Bauer et al, 2000; and Nieminen et al, 2000), for which volatile biomarkers in patient breath have been identified. Nitric oxide (NO) is another analyte in exhaled breath and it can be used as a biomarker for asthma (Alving et al, 1993).

Twenty-two million people in the US have been diagnosed with asthma (CDC, 2008), yet the tools available for monitoring asthma are limited. A few simple tools are available for in-home use that can provide some indication of lung health. Peak flow meters, for example, can measure one's peak expiratory flow rate (PEFR), and spirometers can measure lung volume and flow. However, abnormal readings from either of these devices can be attributed to a variety of causes other than asthma, and these techniques may not be predictive of onset of an acute asthmatic attack, nor provide immediate feedback on the effect of a therapeutic intervention. A better approach is to monitor nitric oxide, a biomarker of asthma, which is exhaled in human breath. The concentration of fractional exhaled nitric oxide (FeNO) is higher in asthmatics than in healthy people. It increases during an asthmatic exacerbation, and decreases following treatment with an inhaled corticosteroid (Smith et al, 2004). A breath analyzer that reliably detects FeNO would allow widespread self-monitoring by the asthmatic population.

In 1991 Gustafsson et al demonstrated the presence of nitric oxide in the exhaled breath of humans. Shortly thereafter it was reported that FeNO levels are elevated in asthmatics compared to that in control subjects (Alving et al, 1993). Since the time of these discoveries there now exist over 1,000 publications (Medline search, December 2007) that implicate nitric oxide as a biomarker of airway inflammation and deliver a vast amount of knowledge on the importance of FeNO measurements. For example, nitric oxide levels in exhaled breath correlate with eosinophil-mediated airway inflammation (van den Toorn et al 2001, Mattes et al 1999, Jatakanon et al 1998). Several investigators have reported that nitric oxide concentrations decrease following use of corticosteroids (Massaro and Drazen; 1996, Yates et al 1995; Silkoff et al 1998; van Rensen, 1999) and that measurements of FeNO can be used as a noninvasive diagnostic for asthma (Pijnenburg, 2005). It has also been shown that FeNO measurements can be used to regulate medications (Smith et al, 2005; Taylor, 2006)

Levels of exhaled nitric oxide can provide feedback for asthma patients and their physicians. While numerous studies have been performed to measure levels of exhaled NO there is little consensus on what the standard level is in healthy subjects. In fact, physiological levels of NO can vary greatly between people. Some of the variability is related to age (Buchvald et al, 2005) and gender (Olivieri et al 2006). However, some of the NO variability can be attributed to the variety of test methods due to the lack of standardized procedures among the testing groups (Müller et al, 2005). None the less, studies report that the levels of FeNO in asthmatics are significantly higher than those in control subjects (Alving et al 1993, and Kharitonov et al, 1994). Several groups have established baseline levels of FeNO in asthmatics and monitored their levels during exacerbations. Jones et al (2001) reported that when steroids were withdrawn a 60% increase in FeNO over baseline predicted a loss of control in asthma 80-90% of the time. In a second study, Jones et al (2002) showed a positive correlation between serial measurements of FeNO and a dose-response to an inhaled steroid. Reports such as these indicate 1) the importance of establishing a baseline for each individual, and 2) that tracking an individual's FeNO levels can be extremely useful in predicting exacerbations and monitoring efficacy of medications.

One of the major problems in completing these assessments is the lack of methods and monitoring devices to measure components from exhaled breath. Several technologies exist that are capable of detecting and monitoring gas-phase compounds including those found in breath. The sensors available and their disadvantages are described here briefly. They are based on technologies that can be categorized into four main classes including: chromatography and spectrometry, electrochemical sensors, mass sensors, and optical sensors. Chromatography and spectrometry involve separation of complex mixtures by passing them over selectively absorptive materials and subsequent analysis of the components. These instruments are gas chromatographs, ion mobility and mass spectrometry (IMS) instruments, and photo-ionization (PIDs) and flame ionization detectors (FIDs). Instruments in this category are benchtop, portable, or miniature (lab on a chip) in size. The general deficiencies of such instruments are that they are prohibitively expensive and technically complicated, require recalibration, most lack portability, require GC for specificity, sensitive to humidity, and require on-board hydrogen gas. Electrochemical sensors detect changes in electrical current passed through an electrode when a chemical reacts with that electrode. Included in this category are polymer-absorption chemiresistors, catalytic bead sensors, metal-oxide semi-conductor sensors, single wall nanotubes (SWNT), and potentiometric and amperometric sensors. In general these instruments have selectivity issues, high drift, and short shelf-life, require internal pump and elevated temperatures for operation, are sensitive to water vapor and to hydrogen. Mass sensors, including surface acoustic wave sensors and microcantilever sensors, detect changes in the profile representing the mass of the chemical. They are prohibitively expensive, susceptible to humidity changes, and not readily transportable. Optical sensors, including fiber optic sensors, colorimetric, (chemical papers, detector tubes), and infrared sensors, detect changes in visible light when a chemical is present. They have limited dynamic range, lack specificity, high rate of false positives, optics impaired by particulates, and sensitive to humidity.

Although many sensors are capable of measuring gases and some are currently used in research applications, few have been adapted for use by the healthcare consumer. In general, hurdles to these sensor technologies include instrumentation that is expensive, requires frequent calibrations and regular maintenance, complicated to operate, large in size, and lacks selectivity for the targeted gas.

LCs have been previously used to detect gas phase compounds. These methods for detecting compounds with liquid crystals are based on reversible or nonreversible interactions between compounds and functional groups on a surface that can detect such interactions. This body of work relies on the interaction of the LC with a functionalized surface, i.e., surface driven detection. The surfaces may be treated with metals (gold, titanium), with self-assembled monolayers (e.g., MBA, MUA), ligands or recognition moieties (metal salt complexes or enzymes), and linkers (homo or hetero-bifunctional) that are used to immobilize the layers. Thus, the technology is first dependent on the fabrication of appropriately functionalized surfaces and secondly dependent on the diffusion of the analyte through the LC layer to the surface so that the interaction between the analyte and the surface may occur. In devices that rely on surface interactions, it is a change of the orientation of the LC pre and post-exposure to the analyte that is measured to determine whether the analyte is present.

What is needed in the art are assays for detection of gas phase compounds that do not rely on complex, expensive equipment or exclusively on the interaction of the analyte with the surface of the device.

SUMMARY OF THE INVENTION

The present invention relates to the field of detection of gas phase compounds, and in particular to detection of nitric oxide exhaled as a component of breath using a liquid crystal assay format and a device utilizing liquid crystals as part of reporting system. Accordingly, in some embodiments, the present invention provides methods of detecting an analyte in a gaseous phasecomprising: a) providing a liquid crystal assay device comprising a substrate having a surface, the surface in contact with a liquid crystal (LC) composition; b) exposing the liquid crystal assay device to a sample suspected of containing the analyte in a gaseous phase; and c) interrogating said liquid crystal assay device to detect said analyte in a gaseous phase, wherein a change in properties of the LC composition in said assay device caused by interaction of said analyte with said liquid crystal composition is indicative of the presence of said analyte. The method of interrogation can be but is not limited to measurement of change in optical anisotropy, measurement of phase transition temperature, measurement of dielectric anisotropy. In some embodiments, the LC composition comprises a reactive moiety. In some embodiments, the reactive moiety is selected from the group consisting of aliphatic alcohol, phenol, ether, aromatic ether, aliphatic aldehydes, benzaldehyde, aliphatic amine, aniline, aliphatic carboxylic acid, benzoic acid, azo, and alkyne. In some embodiments, interaction of the analyte in a gaseous phase with the LC composition that is indicative of the presence of said analyte is related to a pressure or temperature change in the presence of said analyte.

In some embodiments, the liquid crystal assay device comprises an array of discrete assay areas, wherein each of said discrete assay areas comprises a LC composition. In some embodiments, the array comprises an internal calibration area and wherein said interrogation step further comprises comparing the differential response between said calibration area and at least one of said discrete assay areas.

In some embodiments, the interrogation step is performed by measuring the change in the optical properties of the LC composition. The present invention is not limited to the use of any particular method of change in optical properties. Indeed, the use of a variety of methods that allows the change in the optical properties of the LC composition is contemplated, including, by measuring the transmission of light (such as visible light, infra-red light or UV light) through the LC composition placed between crossed polarizers and the transmitted light from the devices is measured by a detector. In some embodiments, the transmitted light from the device exhibits a maxima that is different in the presence of the gaseous compound than in its absence. In other embodiments, the transmitted light from the device exhibits a spectrum that is different in the presence of the gaseous compound than in the absence of the gaseous compound. In still other embodiments, the radiation returned from the device exhibits a change in the intensity of the peak of the spectrum emitted from the device.

In some embodiments, the liquid crystal assay device comprises a wave guide on a substrate or optical fiber surrounded by the LC composition. In further embodiments, the wavelength and/or intensity of light transmitted through the waveguide is different in the presence the analyte in a gaseous phase than in the absence of the analyte in a gaseous phase. In some embodiments, the device comprises two identical optical waveguide paths that give a maximum intensity of light at a given wavelength. In further embodiments, when light passes through these optical paths the wavelength and or intensity of light transmitted through the waveguide is different in the presence the gaseous compound than in the absence of the gaseous compound. In further embodiments, the interaction of the analyte with the LC composition causes a change in the light returned from the device upon irradiation.

In some embodiments, the interrogation step is performed by measuring the change in dielectric properties of the LC composition. The present invention is not limited to the use of any particular method of change in dielectric properties. Indeed, the use of a variety of methods that allows the change in the dielectric properties of the LC composition is contemplated, including, by measuring the electrical capacitance of a thin film of the LC composition. In some embodiments, a thin film of the LC composition is supported between a solid substrate with gold electrodes and another permeable membrane with identical electrodes. These two electrodes are aligned with each other and the electrical capacitance of the LC composition between these two electrodes is different in the presence of the gaseous compound than in its absence. The present invention is not limited to any particular thickness of the film of the LC composition. In some embodiment it could be less than 100 micron and in some other embodiments it could be less than 1 micron. In other embodiments, a thin film of the LC composition is supported on a substrate with interdigitated microelectrodes and the capacitance of the film of the LC composition is different in the presence of the gaseous compound than in the absence of the gaseous compound. The present invention is not limited to any particular numbers and dimensions of the interdigitated electrodes. Indeed, the number could be 10-500 and the length of the electrodes could be 10 micron-1 cm and the width of the electrodes could be 1 micron to 100 micron. The present invention is not limited to a particular thickness of the LC composition. Indeed the thickness of the LC composition film could be less than 100 micron. In some embodiments, the electrodes are from 100 angstroms to 500 angstroms high, 2 microns to 100 microns wide and spaced 2 microns to 100 microns apart. In some embodiments, the electrodes are from 2 microns to 10 microns high, 2 microns to 100 microns wide, and spaced 2 microns to 100 microns apart. In some embodiments, the electrodes form interdigitated channels In some embodiments, the electrodes are in a planar configuration. However, the electrodes are not limited to planar configuration. Indeed other possible configurations have been contemplated, including, but not limited to, cylindrical configurations.

In some embodiments, the electrodes are less than 5 microns thick and the spacing between them is less than 10 microns. In one embodiment, the LC composition is filled in the cavity formed between two concentric cylinders. The outer cylinder is comprised of a permeable membrane. The electrical capacitance between these two cylinders changes upon exposure to the gases.

The present invention is not limited to the use of devices with particular types of surfaces. Indeed, the use of a variety of surface materials is contemplated, including, but not limited to gold, glass and silicon. In some embodiments, the surface (gold, glass or silicon) is functionalized by chemical treatment (for example by addition of a self-assembled monolayers or gold, silane treatment on glass or silicon). In some embodiments, the functionalized surface promotes wetting by liquid crystals. In some embodiments, the functionalized surface aligns mesogens. In some embodiments, the functionalized surface reduces the anchoring energy of the mesogens so that the interaction of the analyte with the LC composition facilitates reorientation of liquid crystals on the surface. In some embodiments, the functionalized surface repels the liquid crystal. In some embodiments, the surface functionalization chemistry is deposited such that delivery of the LC composition to the substrate results in a patterned distribution of areas wetted with the LC composition and areas void of the LC composition.

The present invention is not limited to any particular liquid crystal assay device format. Indeed, a variety of formats are contemplated, including, but not limited to planar, spherical, and cylindrical formats. In some embodiments, the surface is a patterned surface. In some embodiments, the patterned surface is defined by physical structures or chemical functionalization or combinations thereof. In some embodiments, patterned surface comprises features selected from the group consisting of a grid, a channel, a plurality of channels, a plurality of pillars, or an array of assay areas or combination thereof. In some embodiments, the features are 1 micron to 200 microns wide, 1 micron to 50 microns high and spaced 1 micron to 200 microns apart. In some embodiments, the pillars comprise a shape selected from the group consisting of circular, triangular, square, hexagonal, or a combination thereof. In some embodiments where the surface is cylindrical so that said device has two ends, one of said ends is open and the other of said ends is closed.

In some embodiments, the liquid crystal assay device comprises patterned silicon. Indeed, it is contemplated that the silicon pattern may include, but is not limited to a grid, a channel, a plurality of channels, a plurality of pillars, and an array of areas shaped as squares, circles, triangles. In some embodiments, the pattern is prepared by photolithographic methods. The present invention is not limited to assay devices of any particular size. Indeed, a variety of sizes are contemplated. In some embodiments, the liquid crystal assay devices are less than 1 cm in width and length, respectively. In other embodiments, the liquid crystal assay devices are less than 1 mm in width and length, respectively.

In some embodiments, the liquid crystal assay devices comprise a silicon cylinder, wherein one end of the cylinder is open and the other end is closed. In some preferred embodiments, the closed-end cylinder is substantially filled with liquid crystal. The dimensions of the cylinder are not limited to a particular size. Indeed, a variety of sizes are contemplated. In some embodiments, the cylinders are uniform in diameter along the length of the cylinder. In other embodiments, the cylinders are wider in diameter at one end than at the other end. In some embodiments, the cylinders have a port for egress of air sample. The present invention is not limited to assay devices of any particular size. Indeed, a variety of sizes are contemplated. In some embodiments, the liquid crystal assay devices are less than 4 cm in width and length, respectively. In other embodiments, the liquid crystal assay devices are less than 1 mm in width and length, respectively.

The present invention is not limited to the use any particular type of mesogen in the LC composition. Indeed, the use of a variety of mesogens is contemplated, including, but not limited to thermotropic, lyotropic, metallotropic, and cholesteric. In some embodiments, the interaction of the liquid crystal with the gaseous compound leads to a phase transition.

In some embodiments, the phase transition is due to a chemical reaction. The chemical reaction is not limited to any particular liquid crystal. A variety of LCs are contemplated including but not limited to MBBA (N-(4-methoxybenzylidene)-4-butylaniline), EBBA (N-4-ethoxybenzylidene)-4-butylaniline) and 4-(trans-4-heptylcyclohexyl)-anilin which have functional groups suitable for reacting with nitrate-based compounds. In some embodiments the functional groups are selected from the group consisting of aliphatic alcohol, phenol, ether, aromatic ether, aliphatic aldehyde, benzaldehyde, aliphatic amine, aniline, aliphatic carboxylic acid, benzoic acid, azo, and alkyne and combinations thereof.

In some embodiments, a mixture of different mesogens in the LC composition is contemplated. In some embodiments, the mixture of mesogens increases the sensitivity of detection by methods including but not limited to improving the partition of target analytes, increasing the wetting property of the film of the LC composition, improving the interaction of analytes with the LC compositions or surface or enhancing the change in physical properties. In some embodiments, the phase transition is due to a physical dilution of the liquid crystal. The phase transition is not limited to any particular order of change. Indeed, a variety of phase changes are contemplated including a phase transition from a higher order to a lower order or vice versa. In some embodiments the thermotropic liquid crystal transitions include, but are not limited to an isotropic phase changing to a nematic phase, a smectic A phase changing to a nematic phase, and a nematic phase changing to an isotropic phase. The present invention is not limited to the use any particular mesogen. Indeed, the use of a variety of mesogens is contemplated, including, but not limited to MBBA, EBBA, MLC-6812, MLC 12200, 5CB (4-n-pentyl-4'-cyanobiphenyl), 8CB (4-cyano-4'octylbiphenyl) and 4-(trans-4-heptylcyclohexyl)-anilin. In some embodiments, the LC composition undergoes an orientational transition in the presence of said analyte selected from the group consisting of homeotropic changing to a planar alignment, random planar alignment changing to uniform planar alignment, uniform planar alignment changing to random planar alignment, and planar alignment changing to homeotropic alignment. In some embodiments, the LC composition undergoes an orientational transition followed by a phase transition in the presence of said analyte.

In some embodiments, a small amount of polar material is added to the LC composition as a dopant. The dopant is not limited to any particular material. Indeed, the use of a variety of dopants is contemplated, including, but not limited to reactive and non-reactive dopants. In some embodiments, the dopant is a substituted aniline compound. In some embodiments, the dopant is a substituted benzidine compound. In some embodiments, the reactive dopants are aniline-based compounds including but not limited to 2-methyl aniline and 3,3'-dimethylbenzidine that react with nitrate-based gaseous compounds and their derivatives. In some embodiments the dopants are materials that enhance the dielectric anisotropy such as ferroelectric nano-particles or carbon nano-tubes. In some embodiments, the dopant is a material that mixes with the LC composition.

In some embodiments, the interaction of the LC composition with the gaseous compound leads to an orientational transition on the device surface. In some embodiments, the interaction of the LC composition with the gaseous compounds leads to a change in physical properties of the LC composition and subsequently an orientational transition on the device surface. These physical changes that will induce the orientational transition of the LC composition include, the change in the elastic constant of the LC composition, the change in wetting properties of the LC composition on a given surface, and the change in the electrical conducting properties of the LC composition.

The instillation of the LC composition onto the substrate of the LC assay device is not limited to deposition by any particular method. In some embodiments, the LC composition is deposited by spin coating to produce a thin film onto the substrate. In some embodiments, the volume of the LC composition and the speed at which the substrate is spun leads to deposition of a thinner film. In some embodiments, the LC composition is deposited directly onto the substrate. In some embodiments, the LC composition is dissolved in a non-aqueous solvent before depositing on the substrate. In some embodiments, the non-aqueous solvent is from the group including but not limited to n-octane, toluene, ethanol, propanol, isopropanol, heptane, hexane, petroleum ether, and carboxylic acid. In some embodiments, the liquid crystal composition is dispensed from devices, including but not limited to micropipette tips, microarrayers, and nanoliter dispensers fitted with metal pins. In some embodiments, the type of instillation from the nanoliter dispenser is from the group including contact and non-contact spotting. In some embodiments, the installation of the LC composition occurs in a temperature and humidity controlled environment. In some embodiments, the temperature and/or humidity of the local environment are varied over the course of the instillation. In some embodiments, the LC composition spreads across the substrate by capillary action. In some embodiments, microstructured features on the substrate augment the spreading of the LC composition. In some embodiments, an agent added to the liquid crystal augments its wetting properties on the substrate. In some embodiments the wetting agent is selected from the group including but not limited to polymers and fumed alumina.

The systems of the present invention are not limited to the detection of any particular gaseous compound. In some embodiments, the analyte is a compound in the breath (exhalation) of a subject. In some embodiments, the compound in the breath (exhalation) of the subject is generated from the cellular metabolism of a drug or substrate. Indeed, the detection of a variety of gaseous compounds in breath or exhalation of a subject is contemplated, including, molecules that are exogenous and endogenous in origin to the subject. In some embodiments, the exogenous molecules are generated from cellular metabolism of a drug or substrate, including but not limited to acetate, aminopyrine, caffeine, erythromycin, ethanol, ethyl glucuronide, galactose, glucose, lactose, glycosyl ureides, ketoisocaproate, linoleic acid, methacetin, methione, phenylalanine, triolein, uracil, and urea. In some embodiments, the endogenous molecules are a result of normal or abnormal physiologies, and include but are not limited to acetaldehyde, acetone, ammonia, carbon disulfide, carbon monoxide, carbonyl sulfide, ethane, ethanol, ethylene, hydrocarbons, hydrogen, isoprene, methane, methanethiol, methanol, methylamine, and pentane. In some preferred embodiments the endogenous molecules are nitric oxide.

The present invention is not limited to direct detection of a breath (exhalation) component. In some embodiments, the gaseous phase is treated. In some embodiments, the treatment is with an agent selected from the group consisting of oxidizing, reducing, and hydrating agents to provide a derivatized analyte. In some embodiments, the oxidizing agent is selected from the group consisting of chromium oxide, dichromate, permanganate, and ozone. In some embodiments, the analyte is nitric oxide that is oxidized to nitrogen dioxide then derivatized to nitrous acid and nitric acid in the presence of humidity prior to said exposing step. Indeed, the detection of a derivative of a breath component is contemplated. In some embodiments, the functional groups of breath components will be subjected to oxidizing, reducing, and hydrating agents leading to derivatized compounds. In some embodiments the oxidizers include, but are not limited to chromium oxide, dichromate, permanganate and ozone. In some preferred embodiments, the nitric oxide in exhaled breath is oxidized to nitrogen dioxide and further derivatized to nitrous acid and nitric acid in the presence of humidity.

In some embodiments, the present invention provides methods of assaying levels of exhaled nitric oxide directly comprising: a) providing a device comprising a surface in contact with a LC composition; and b) exposing the device to a breath sample suspected of containing nitric oxide, wherein presence of nitric oxide is indicated by a change in the properties of said LC composition. The present invention is not limited to the use of any particular liquid crystal. Indeed, the use of a variety of liquid crystal compositions is contemplated, including, but not limited to those selected from the group consisting of 5CB, MBBA, EBBA, MLC-6812, and MLC 12200. In some embodiments, the liquid crystals are arranged in channels on the device surface. In some preferred embodiments, the identity of nitric oxide is discernable from the phase transition of liquid crystals on the channels. In still other embodiments, the exposing step is from about 1 second to about 10 hours in length. In some embodiments, exhaled nitric oxide is reacted with an oxidizing agent to provide nitric oxide derivatives; and exposing said device to said nitric oxide derivatives, wherein presence of nitric oxide is indicated by a change in the properties of the LC composition.

In some embodiments, the present invention provides methods of assaying levels of exhaled nitric oxide indirectly comprising: a) providing a device comprising a surface in contact with a LC composition; and b) exposing the device to a breath sample suspected of containing nitric oxide, wherein presence of nitric oxide derivatives are indicated by a change in the phase of the liquid crystal identified as a change in the physical parameters of the LC composition. The present invention is not limited to the use of any particular liquid crystal. Indeed, the use of a variety of liquid crystal compositions is contemplated, including, but not limited to those selected from the group consisting of 5CB, MBBA, EBBA, MLC-6812, and MLC 12200. In some embodiments, the liquid crystals are arranged in channels on the device surface. The represent invention is not limited to the use of any particular oxidizer. Indeed, the use of a variety of oxidizing agents is contemplated, including, but not limited to those selected from the group consisting of chromium oxide, dichromate, and permanganate. In some preferred embodiments, the identity of nitric oxide derivatives is discernable from the phase transition of liquid crystals on the channels. In still other embodiments, the exposing step is from about 1 second to about 10 hours in length.

In some embodiments, the present invention provides methods of assaying levels of exhaled nitric oxide directly comprising: a) providing a device comprising a LC composition, the LC composition provided in bulk, the bulk of the LC composition substantially filling a reservoir, the device having an opening therein; and b) exposing the device to a breath sample suspected of containing nitric oxide, wherein presence of nitric oxide is indicated by a change in the phase of the LC composition identified as a transition of the bulk of the LC composition. The present invention is not limited to the use of any particular liquid crystal. Indeed, the use of a variety of liquid crystal compositions is contemplated, including, but not limited to those selected from the group consisting of 5CB, MBBA, EBBA, MLC-6812, and MLC 12200. In some embodiments, the LC composition is arranged in separate reservoirs in the device. In some preferred embodiments, the identity of nitric oxide is discernable from the phase transition of LC composition in the reservoirs. In still other embodiments, the exposing step is from about 1 second to about 10 hours in length.

In some embodiments, the present invention provides methods of assaying levels of exhaled nitric oxide indirectly comprising: a) providing a device comprising a LC composition, the LC composition provided in bulk, the bulk of the LC composition substantially filling a reservoir, the device having an opening therein, an oxidizing agent provided downstream of the opening and upstream of the LC composition; and b) exposing the device to a breath sample suspected of containing nitric oxide, wherein presence of nitric oxide derivatives are indicated by a change in the phase of the LC composition identified as a transition of the bulk of the LC composition. The present invention is not limited to the use of any particular liquid crystal. Indeed, the use of a variety of LC compositions is contemplated, including, but not limited to those selected from the group consisting of 5CB, MBBA, EBBA, MLC-6812, and MLC 12200. In some embodiments, the LC composition is arranged in channels on the device surface. The represent invention is not limited to the use of any particular oxidizer. Indeed, the use of a variety of oxidizing agents is contemplated, including, but not limited to those selected from the group consisting of chromium oxide, dichromate, permanganate, and ozone. In some preferred embodiments, the identity of nitric oxide derivatives is discernable from the phase transition of LC composition in the reservoirs. In still other embodiments, the exposing step is from about 1 second to about 10 hours in length.

In other embodiments, the present invention provides methods of identifying a particular breath component comprising: a) providing a substrate comprising at least two detection regions having at least two different LC compositions deposited thereon; and b) exposing the device to a sample suspected of containing a breath component; and c) determining the identity of the breath component by examining the change in properties of the LC composition in the detection regions. In some embodiments, the LC composition overlaying the detection regions is nematic in the presence of the breath component. In further embodiments, the detection region has deposited thereon a plurality of different LC compositions selected from the group consisting of 5CB, MBBA, EBBA, MLC-6812, and MLC 12200. In further embodiments, the exposing step is from about 1 second to about 10 hours in length. In still further embodiments, the change in phase is indicated by an advancing wavefront. In still other embodiments, the advancement of the wavefront correlates to exposure to breath components. In some embodiments, the detection region comprises a closed-end cylinder and said liquid crystal is delivered in bulk. In further embodiments, the LC composition is diluted by addition of a dopant. In other embodiments, the methods comprise further providing an oxidizing agent downstream of the opening and upstream of the LC reservoir.

In still further embodiments, the present invention provides devices comprising: at substrate having a surface, said substrate further comprising at least a first detection region on said surface, wherein said detection region comprises a liquid crystal composition that interacts with an analyte in a gaseous phase; and a housing having an opening therein, said substrate configured in said housing so that said detection region is exposed to the atmosphere through said opening. In some embodiments, the housing is movable between an exposure position wherein the detection region is exposed to the atmosphere through the opening and a reading position wherein said detection region is substantially closed off to the atmosphere. In some embodiments, the devices further comprise a filter in the opening. In some preferred embodiments, the filter is an aerosol filter. In some embodiments, the devices further comprise an oxidizing agent downstream of the opening. In some preferred embodiments, the oxidizer is permanganate. In some preferred embodiments, the detection region is configured to contain a LC composition. In some embodiments, the LC composition is selected from the group consisting of 5CB, MBBA, EBBA, MLC-6812, and MLC 12200. In some embodiments, the detection region provides channels. In some embodiments, the LC composition is deposited as a layer in the channels. In still other embodiments, the devices comprise a closed-end cylinder receiving a LC composition. In some embodiments, the substrate comprises a plurality of distinct detection regions. In further embodiments, the plurality of distinct detection regions comprises at least two different recognition moieties.

DESCRIPTION OF THE FIGURES

FIG. 1 describes characteristics of liquid crystals deposited on the sensor array.

FIG. 2 is an image of an array template (A) with spots corresponding to LCs listed in FIG. 1 and images of the LC-sensor array at t=0 (B) and 25 (C) minutes following exposure to nitric acid.

FIG. 3 describes characteristics of liquid crystals deposited on the sensor array.

DEFINITIONS

Figure 4:
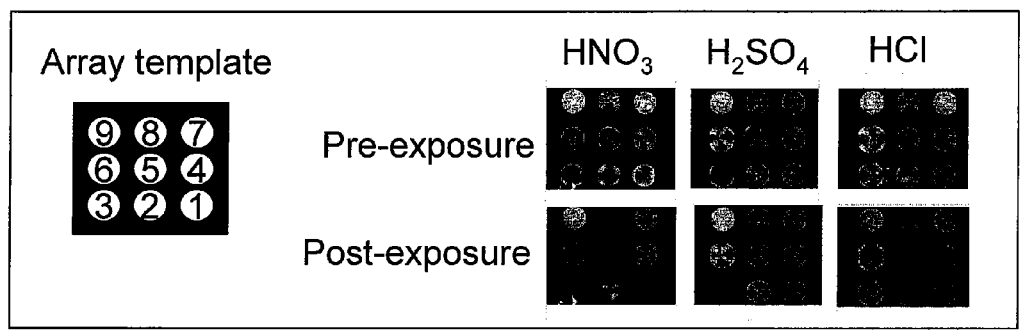
FIG. 4 is an image of an array template (left) with spots corresponding to LCs listed in FIG. 3 and images of the LC-sensor array pre and post-exposure to nitric acid, hydrochloric acid, and sulfuric acid.

As used herein, the term "organophosphate" refers to phosphorous containing organic compounds.

As used herein, the term "wavefront" refers to a line of demarcation that is observable between a region of ordered liquid crystal and a region of disordered liquid crystal. In many cases, the wavefront is visually detectable. However, the location of the wavefront can also be detected by image analysis procedures.

As used herein, the term "ligand" refers to any molecules that binds to or can be bound by another molecule.

As used herein, the term "detection region" refers to a discreet area on substrate that is designated for detection of an analyte (e.g., an organophosphate) in a sample.

As used herein, the terms "material" and "materials" refer to, in their broadest sense, any composition of matter.

As used herein, the terms "field testing" refers to testing that occurs outside of a laboratory environment. Such testing can occur indoors or outdoors at, for example, a worksite, a place of business, public or private land, or in a vehicle.

As used herein, term "nanostructures" refers to microscopic structures, typically measured on a nanometer scale. Such structures include various three-dimensional assemblies, including, but not limited to, liposomes, films, multilayers, braided, lamellar, helical, tubular, and fiber-like shapes, and combinations thereof. Such structures can, in some embodiments, exist as solvated polymers in aggregate forms such as rods and coils. Such structures can also be formed from inorganic materials, such as prepared by the physical deposition of a gold film onto the surface of a solid, proteins immobilized on surfaces that have been mechanically rubbed, and polymeric materials that have been molded or imprinted with topography by using a silicon template prepared by electron beam lithography.

As used herein, the terms "self-assembling monomers" and "lipid monomers" refer to molecules that spontaneously associate to form molecular assemblies. In one sense, this can refer to surfactant molecules that associate to form surfactant molecular assemblies. The term "self-assembling monomers" includes single molecules (e.g., a single lipid molecule) and small molecular assemblies (e.g., polymerized lipids), whereby the individual small molecular assemblies can be further aggregated (e.g., assembled and polymerized) into larger molecular assemblies.

As used herein, the term "linker" or "spacer molecule" refers to material that links one entity to another. In one sense, a molecule or molecular group can be a linker that is covalent attached two or more other molecules (e.g., linking a ligand to a self-assembling monomer).

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., C—C). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds. As used herein the terms "amine bond," "thiol bond," and "aldehyde bond" refer to any bond formed between an amine group (i.e., a chemical group derived from ammonia by replacement of one or more of its hydrogen atoms by hydrocarbon groups), a thiol group (i.e., sulfur analogs of alcohols), and an aldehyde group (i.e., the chemical group —CHO joined directly onto another carbon atom), respectively, and another atom or molecule.

As used herein, the term "covalent bond" refers to the linkage of two atoms by the sharing of two electrons, one contributed by each of the atoms.

As used herein, the term "optical anisotropy" refers to the different optical properties of the liquid crystals for different polarization directions. The anisotropy in optical properties of liquid crystals gives rise to optical birefringence that is the refractive indices of liquid crystals measured with different polarization directions are different.

As used herein, the term "magnetic anisotropy" refers to the different magnetic properties of the liquid crystals for different directions of magnetic fields. The anisotropy in magnetic properties of liquid crystals gives rise to magnetic anisotropy that is the magnetic susceptibilities of liquid crystals measured with different magnetic field directions are different.

As used herein, the term "dielectric anisotropy" refers to the different dielectric properties of the liquid crystals for different directions of electric fields. The anisotropy in dielectric properties of liquid crystals gives rise to dielectric anisotropy that is the dielectric constant of liquid crystals measured with different electric field directions are different.

As used herein, the term "spectrum" refers to the distribution of light energies arranged in order of wavelength.

As used the term "visible spectrum" refers to light radiation that contains wavelengths from approximately 360 nm to approximately 800 nm.

As used herein, the term "substrate" refers to a solid object or surface upon which another material is layered or attached. Solid supports include, but are not limited to, glass, metals, gels, and filter paper, among others.

As used herein, the terms "array" and "patterned array" refer to an arrangement of elements (i.e., entities) into a material or device. For example, depositing several types of liquid crystals into discrete regions on an analyte-detecting device, would constitute an array.

As used herein, the term "in situ" refers to processes, events, objects, or information that are present or take place within the context of their natural environment.

As used herein, the term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

As used herein, the term "liquid crystal" refers to a thermodynamic stable phase characterized by anisotropy of properties without the existence of a three-dimensional crystal lattice, generally lying in the temperature range between the solid and isotropic liquid phase.

As used herein, the term "mesogen" refers compounds that form liquid crystals, including rodlike or disclike molecules which are components of liquid crystalline materials.

As used herein, "thermotropic liquid crystal" refers to liquid crystals which result from the melting of mesogenic solids due to an increase in temperature. Both pure substances and mixtures form thermotropic liquid crystals.

"Lyotropic," as used herein, refers to molecules which form phases with orientational and/or positional order in a solvent. Lyotropic liquid crystals can be formed using amphiphilic molecules (e.g., sodium laurate, phosphatidylethanolamine, lecithin). The solvent can be water.

"Metallotropic," as used herein, refers to metal complexes of organic ligands which exhibit liquid crystalline character. Thermotropic metallomesogens have been made that incorporate many metals. They can be rodlike (calamitic) and disklike (discotic). The ligand can be monodentate (4-substituted pyridines), bidentate (β-diketonates, dithiolenes, carboxylates, cyclometalated aromatic amines), or polydentate (phthalocyanines, porphyrins). The ligands influence the mesophase character based on molecular shape and intermolecular forces. The metallomesogens provide a rigid core, typically unsaturated and either rod- or disklike in shape; and several long hydrocarbon tails where the metal atom is usually at or near the center of gravity of the molecule. Metallotropic liquid crystals, acting through the metal moiety, can be tuned to capture different target analytes by different methods including but not limited to displacement, redox reactions, and ligand formation.

As used herein, the term "heterogenous surface" refers to a surface that orients liquid crystals in at least two separate planes or directions, such as across a gradient.

As used herein, "nematic" refers to liquid crystals in which the long axes of the molecules remain substantially parallel, but the positions of the centers of mass are randomly distributed. Nematic liquid crystals can be substantially oriented by a nearby surface.

"Chiral nematic," as used herein refers to liquid crystals in which the mesogens are optically active. Instead of the director being held locally constant as is the case for nematics, the director rotates in a helical fashion throughout the sample. Chiral nematic crystals show a strong optical activity that is much higher than can be explained on the bases of the rotatory power of the individual mesogens. When light equal in wavelength to the pitch of the director impinges on the liquid crystal, the director acts like a diffraction grating, reflecting most and sometimes all of the light incident on it. If white light is incident on such a material, only one color of light is reflected and it is circularly polarized. This phenomenon is known as selective reflection and is responsible for the iridescent colors produced by chiral nematic crystals.

"Smectic," as used herein refers to liquid crystals which are distinguished from "nematics" by the presence of a greater degree of positional order in addition to orientational order; the molecules spend more time in planes and layers than they do between these planes and layers. "Polar smectic" layers occur when the mesogens have permanent dipole moments. In the smectic A2 phase, for example, successive layers show anti ferroelectric order, with the direction of the permanent dipole alternating from layer to layer. If the molecule contains a permanent dipole moment transverse to the long molecular axis, then the chiral smectic phase is ferroelectric. A device utilizing this phase can be intrinsically bistable.

"Frustrated phases," as used herein, refers to another class of phases formed by chiral molecules. These phases are not chiral, however, twist is introduced into the phase by an array of grain boundaries. A cubic lattice of defects (where the director is not defined) exist in a complicated, orientationally ordered twisted structure. The distance between these defects is hundreds of nanometers, so these phases reflect light just as crystals reflect x-rays.

"Discotic phases" are formed from molecules which are disc shaped rather than elongated. Usually these molecules have aromatic cores and six lateral substituents. If the molecules are chiral or a chiral dopant is added to a discotic liquid crystal, a chiral nematic discotic phase can form.

DESCRIPTION OF THE INVENTION

The present invention relates to the field of detection of gaseous compounds, and in particular to detection of exhaled nitric oxide, a component of breath, using a liquid crystal assay format and a device utilizing liquid crystals as part of a reporting system. Liquid crystal-based assay systems and devices (LC assays) are described in U.S. Pat. No. 6,284,197; WO 01/61357; WO 01/61325; WO 99/63329; Gupta et al., Science 279:2077-2080 (1998); Seung-Ryeol Kim, Rahul R. Shah, and Nicholas L. Abbott; Orientations of Liquid Crystals on Mechanically Rubbed Films of Bovine Serum Albumin: A Possible Substrate for Biomolecular Assays Based on Liquid Crystals, Analytical Chemistry; 2000; 72(19); 4646-4653; Justin J. Skaife and Nicholas L. Abbott; Quantitative Interpretation of the Optical Textures of Liquid Crystals Caused by Specific Binding of Immunoglobulins to Surface-Bound Antigens, Langmuir; 2000; 16(7); 3529-3536; Vinay K. Gupta and Nicholas L. Abbott; Using Droplets of Nematic Liquid Crystal To Probe the Microscopic and Mesoscopic Structure of Organic Surfaces, Langmuir; 1999; 15(21): 7213-7223; and Shah and Abbott, Principals for Measurement of Chemical Exposure Based on Recognition-Driven Anchoring Transitions in Liquid Crystals, Science 293:1296-99 (2001); all of which are incorporated herein by reference.

U.S. Pat. No. 6,284,197 and Shah and Abbott, supra, describe the detection of chemical molecules, including organophosphates, with a liquid crystal assay format that relies on an orientational change in the LC following the interaction of the chemical with a functionalized surface on which the LC has been overlaid. Interestingly, it has now been discovered that liquid crystal assays can be used for the detection of gaseous compounds and that the compound interacts directly or indirectly with the LC resulting in a phase transition of the material. Additionally, the change in the property of film of LC supported on a surface can also induce a change in orientation of LC on the surface. The use of different LCs that provide different functional moieties/reactive groups, or the use of dopant and LC compositions, in the assays can be lead to the identification of gaseous compounds through the ability of the gaseous compound to interaction with a variety of functional moieties on the LC and/or the dopant. Furthermore, the liquid crystal assay devices of the present invention can be used to quantitate exposure to gaseous compounds.

In some embodiments, the detection of analytes or their derivatives in gas phase is accomplished through a direct interaction with LCs. Depending upon the target analyte, LCs can be synthesized that have different functional groups targeted to interact or react with the analyte. The liquid crystal can either be supported on a surface or in a small bulk amount through which the analyte is passed. The present invention is not limited to the detection of any particular analyte in gas phase. Indeed, the detection of a variety of analytes is contemplated. One exemplary analyte is nitric oxide. It is known that nitric oxide can be efficiently converted to nitrogen dioxide by passing it through chemical oxidizing agents including $KMnO_4$, $K_2Cr_2O_7$, $CrO_3$ etc., or by mixing nitric oxide with other gases such as ozone, or by illuminating the mixture of nitric oxide and oxygen with ultraviolet light. The nitrogen dioxide can then be converted to the more easily detectable nitric or nitrous acid. These derivatives of nitrogen oxide can interact with LC materials provided that the proper functional moieties are available or the target analytes interact directly with LC. For example 2-methyl aniline and 3,3'-dimethylbenzidine are known to interact with nitric acid (The American Water Works Association, 26, 1645, 1934), nitrite (The American Water Works Association, 26, 634, 1934) and blood glucose (Nature, 183, 1959). A number of LCs with different functional moieties are commercially available. Some of these LCs have suitable reactive moieties that are selective for some target analytes. For example, MBBA (N-(4-Methoxybenzylidene)-4-butylaniline and EBBA (N-(4-Ethoxybenzylidene)-4-butylaniline) have functional groups similar to the aniline group that can be used for detection of nitrate-based gases. A number of azomethine-type LCs (H. Hioki et al./Tetrahedron Letters 45 (2004) 7591-7594), polyaniline-based polymers (*J. Phys. Chem. B* 2004, 108, 8894-8899) and polyaniline-based moieties and polyimides [Journal of Polymer Science: Part A: Polymer Chemistry, Vol. 40, 1583-1593 (2002)] have been synthesized. The interaction between the analyte and the LC can be physical in nature or based on chemical reactions. The interaction of the target analytes with the LCs can manifest as a change in the physical properties of LCs (phase transition temperature, optical birefringence, dielectric anisotropy, magnetic anisotropy or even change in the orientation of LCs on a surface) that can be detected using a variety of instruments capable of detecting these physical changes.

In practice, prior art assessment of exhaled nitric oxide has involved use of capturing a portion of exhaled breath "off-line" in an inflatable reservoir and subsequently analyzing the sample via complex instrumentation. Instruments, such as gas chromatographs, ion mobility and mass spectrometry devices can detect and quantify components of breath but they must be operated by highly trained personnel within dedicated facilities and they require maintenance and calibration. Recently, clinical researchers have become interested in analyzing breath samples and newer technology advances are available for such use. In these assessments the "gold standard" is on-line, direct measurement of the breath sample (i.e., no intermediate reservoir).

The current clinical standard for measuring a patients exhaled nitric oxide levels is the NIOX FENO Analyzer (Aerocrine; Sweden). Approved in 2003 by the US FDA (Bates and Silkoff, 2004) it generates ozone which reacts with the NO to produce a chemiluminescent emission. That emission is detected by a photomultiplier tube and conveyed as a signal that is proportional to the input concentration of NO. Other instruments are commercially available that use this technology (GE/Sievers, Eco Physics and Ionics Instruments) but they have not met FDA approval for clinical use. The NIOX instrument is complex, non-portable (88 pounds), and expensive. It requires on-site calibration, limiting its setting suitability, but has found acceptance by clinical research physicians where it is used under the guidance of laboratory professionals.

This invention encompasses the use of a liquid crystal phase transition to measure gases, such as nitric oxide. The assay is simple to perform so that the analysis can be done at the collection site. It should be noted that while exhaled nitric oxide has been described here by way of example, the invention is equally suited for measuring other compounds in gas phase such as but not limited to small and large organics, sulfur-containing compounds, amines, thiols, alcohols, acids, oxides, and phosphates.

In preferred embodiments, the devices of the present invention measure compounds in gas phase, which lends itself to on-line monitoring without the need for intermediate reservoirs. The present invention is not limited to any particular mechanism of action. Indeed, an understanding of the mechanism of action is not necessary to practice the present invention. Nevertheless, it is contemplated that the measurement of gas phase compounds provides an accurate reflection of the concentration of the compound in the environment (ambient air or exhaled breath).

Accordingly, the present invention provides improved substrates and devices for the detection of gaseous compounds. For convenience, the description of the present invention is divided into the following sections: I. Analytes; II. Reactive Moieties; III. Substrates; IV. Mesogens; V. Detection of Gas Phase Compounds; VI. Breath Monitors.

I. Analytes

The methods and devices of the present invention can be used to detect a variety of analytes in the gas phase. The present invention is not limited to the detection of any particular type of analyte. Exemplary analytes include, but are not limited to, sulfur compounds, nitrogen compounds, thiols, alcohols, acids, oxides and phosphates.

The present invention finds use in the detection of variety of sulfur compounds. In some embodiments, the sulfur compounds are from a group that includes sulfides, disulfides, sulfites or sulfates, including but not limited to hydrogen sulfide, Chloromethyl trifluoromethyl sulfide, Ethylene sulfide, Dimethyl sulfide, Methyl Sulfide, Propylene sulfide, Trimethylene sulfide, 2-Chloroethyl methyl sulfide, 2-(Methylthio)ethanol, Ethyl methyl sulfide, Bis(methylthio)methane, 2-(Methylthio)ethylamine, N-Methyl-1-(methylthio)-2-nitroethenamine, Allyl methyl sulfide, 2-Chloroethyl ethyl sulfide, 3-(Methylthio)-1-propanol, 2,2'-Thiodiethanol, 2,2'-Dithiodiethanol, Diethyl sulfide, Methyl propyl disulfide, Tris(methylthio)methane, 2-(Ethylthio)ethylamine, 3-(Methylthio)propylamine, Cystamine dihydrochloride, 4-(Methylthio)-1-butanol, tent-Butyl methyl sulfide, Cyclohexene sulfide, Diallyl sulfide, Allyl disulfide, 3,3'-Thiodipropanol, 3,3'-Thiodipropanol, 3,6-Dithia-1,8-octanediol, Dipropyl sulfide, Isopropyl sulfide, Dipropyl disulfide, Isopropyl disulfide, 4-(Trifluoromethylthio)bromobenzene, 4-(Trifluoromethylthio)phenol, Phenyl trifluoromethyl sulfide, 3,5-Dichlorothioanisole, Chloromethyl 4-chlorophenyl sulfide, 4-(Trifluoromethylthio)aniline, 2-Bromothioanisole, 3-Bromothioanisole, 4-Bromothioanisole, 2-Chlorothioanisole, 3-Chlorothioanisole, 4-Chlorothioanisole, Chloromethyl phenyl sulfide, 2-Fluorothioanisole, 4-Fluorothioanisole, 4-Nitrothioanisole, Thioanisole, 2-(Methylthio)aniline, 3-(Methylthio)aniline, 4-(Methylthio)aniline, 2-(Methylthio)cyclohexanone, 3-(Methylthio)-1-hexanol, 4-(Trifluoromethylthio)benzyl bromide, 4-(Trifluoromethylthio)benzyl alcohol, Phenyl vinyl sulfide, 4-(Methylthio)benzyl bromide, 2-Chloroethyl phenyl sulfide, 4-(Methylthio)benzyl chloride, 2-Methoxythioanisole, 2-(Phenylthio)ethanol, 4-Methoxythioanisole, 4-(Methylthio)benzyl alcohol, Methoxymethyl phenyl sulfide, Ethyl phenyl sulfide, Methyl p-tolyl sulfide, Dibutyl sulfide, Dibutyl disulfide, Bis(trimethylsilylmethyl) sulfide, Phenyl propargyl sulfide, (4-Chlorophenylthio)acetone, Benzyl 2,2,2-trifluoroethyl sulfide, 4'-(Methylthio)acetophenone, Allyl phenyl sulfide, Cyclopropyl phenyl sulfide, 2-Nitro-5-(propylthio)aniline, S-Benzylcysteamine hydrochloride, Isoamyl sulfide, 4'-Methylthioisobutyrophenone, Pentafluorophenyl sulfide, Bithionol, Bis(3,5-dichlorophenyl)disulfide, Bis(3,5-dichlorophenyl)disulfide, Bis(4-chlorophenyl)disulfide, 3-Nitrophenyl disulfide, 4-Nitrophenyl disulfide, Bis(2-nitrophenyl) disulfide, 2-Nitrophenyl phenyl sulfide, 4-Nitrophenyl phenyl sulfide, 2-(4-Chlorophenylthio)aniline, 4-Amino-4'-nitrodiphenyl sulfide, 3,3'-Dihydroxydiphenyl disulfide, Diphenyl sulfide, Diphenyl disulfide, Phenyl disulfide, 2-(Phenylthio)aniline, 2,2'-Diaminophenylsulfide, 4,4'-Diaminodiphenyl sulfide, 2,2'-Dithiodianiline, Hexyl sulfide, Benzyl phenyl sulfide, Bis(phenylthio)methane, Dodecyl methyl sulfide, 2-Nitro-p-tolyl disulfide, Bis(4-methoxyphenyl)disulfide, Dibenzyl sulfide, Dibenzyl disulfide, p-Tolyl disulfide, Benzyl trisulfide, 2-[2-(Aminomethyl)phenylthio] benzyl alcohol, Phenylacetyl disulfide, Dioctyl sulfide, Chlorotriphenylmethyl disulfide, Tris(phenylthio)methane, Tris (phenylthio)methane, Dodecyl sulfide, Hexakis[(4-methylphenyl)thio]benzene, and Hexakis(benzylthio) benzene, Potassium methyl sulfate, Formaldehyde-sodium bisulfite adduct, Methyl sulfate sodium salt, Glyoxal bis(sodium hydrogen sulfite) adduct hydrate, Ethylene sulfite, Glyoxal sodium bisulfite addition compound hydrate, Dimethyl sulfite, Diethyl sulfite, Glutaraldehyde sodium bisulfite addition compound, Dipropyl sulfate, 4-Acetylphenyl sulfate potassium salt, Sodium 2-ethylhexyl sulfate, Sodium octyl sulfate, Dibutyl sulfate, 4-Hydroxy-3-methoxyphenylglycol sulfate potassium salt, Sodium dodecyl sulfate, Ammonium lauryl sulfate solution, Tetradecyl sulfate sodium salt, and Octadecyl sulfate sodium salt. In some embodiments the sulfur compounds are from a group that includes triflates such as but limited to (Trimethylsilyl)methyl trifluoromethanesulfonate, (Trimethylsilyl)methyl trifluoromethanesulfonate, 4-Nitrophenyl trifluoromethanesulfonate, Phenyl trifluoromethanesulfonate, 1-Cyclohexenyl trifluoromethanesulfonate, Catechol bis(trifluoromethanesulfonate), p-Tolyl trifluoromethanesulfonate, 4-Acetylphenyl trifluoromethanesulfonate, 2,6-Dimethoxyphenyl trifluoromethanesulfonate, 3,5-Dimethoxyphenyl trifluoromethanesulfonate, 2-(Trimethylsilyl)phenyl trifluoromethanesulfonate, Di-tert-butylsilyl bis(trifluoromethanesulfonate), 1-Naphthyl trifluoromethanesulfonate, 2-Naphthyl trifluoromethanesulfonate, 4,4'-Biphenol bis(trifluoromethanesulfonate), 3,5-Di-tent-butylphenyl trifluoromethanesulfonate, 1,1'-Bi-2-naphthol bis(trifluoromethanesulfonate). In some embodiments, the sulfur is in an oxidized state, including but not limited to sulfur dioxide, sulfur trioxide, sulfuric acid, sulfur oxide, Methyl phenyl sulfoxide, Phenyl vinyl sulfoxide, Methyl p-tolyl sulfoxide, Butyl sulfoxide, Methyl 2-phenylsulfinylacetate, Diphenyl sulfoxide, p-Tolyl sulfoxide, Dodecyl methyl sulfoxide, and Dibenzyl sulfoxide. In other embodiments, the sulfur is in a compound with halogenated elements, such as sulfenyl halides, sulfinyl halides, and sulfonyl halides including but not limited to Chlorocarbonylsulfenyl chloride, Methoxycarbonylsulfenyl chloride, 2,4-Dinitrobenzenesulfenyl chloride, 4-Nitrobenzenesulfenyl chloride, Trichloromethanesulfinyl chloride, tert-Butylsulfinyl chloride, 2,4,5-Trichlorobenzenesulfonyl chloride, 3,4-Dichlorobenzylsulfonyl chloride, 2-Chlorobenzylsulfonyl chloride, Trichloromethanesulfonyl chloride, Methanesulfonyl fluoride, Chlorosulfonylacetyl chloride, N,N-Dimethylsulfamoyl chloride, Cyclopropanesulfonyl chloride, 2-Propanesulfonyl chloride, Perfluoro-1-butanesulfonyl fluoride, 2-Bromo-4,6-difluorobenzenesulfonyl chloride, 2,3,4-Trichlorobenzenesulfonyl chloride, 2,5-Dibromobenzenesulfonyl chloride, Benzene-1,3-disulfonyl chloride, Cyclohexanesulfonyl chloride, m-Toluenesulfonyl chloride, disulfur dichloride, sulfur hexafluoride, thionyl chloride, and sulfuryl chloride.

In some embodiments, the gas compound contains nitrogen, including but not limited to nitrogen, ammonia, 1,3,5-Trinitrobenzene (TNB), Methyl nitrate, Nitroglycerin (NG), Triaminotrinitrobenzene (TATB), and Pentaerythritol tetranitrate (PETN). In some embodiments, the nitrogen containing compound is an amine. The amine may have an alkyl or an aryl functional group, may be aliphatic or aromatic in structure, may be represented by an organic compound that is a primary, secondary or tertiary amine including but not limited to methylamine, ethanolamine, trisamine, dimethylamine, methylethanolamine, aziridine, azetidine, pyrrolidine, piperidine, trimethylamine, dimethylethanolamine, aniline, cadaverine, idole, putrescine, and bis-tris methane.

In some embodiments, the gas compound is a thiol, including but not limited to methanethiol, ethanethiol, cysteine, 2-mercaptoethanol, dithiothreitol, and 2-mercaptoindole.

In some embodiments, the gas compound is an alcohol. The alcohol may be cyclic or acyclic, may be represented by an organic compound that is a primary, secondary or tertiary alcohol including but not limited to methanol, ethanol, isopropanol, tert-butyl alcohol, propanol, cyclopropanols, cyclobutanols, cyclopentanols, cyclopropanols, cyclohexanol, cycloheptanols, benzylic alcohols, diarylmethanols, and allylic alcohols.

In some embodiments, the gas compound is an acid. The acid may be organic or inorganic, monoprotic, diprotic or triprotic, including but not limited to acetic acid, sulfuric acid, hydrochloric acid, hypochlorous acid, chorous acid, chloric acid, perchloric acid, hydrobromic acid, hydroiodic acid, hydrofluoric acid, nitric acid, nitrous acid, carbonic acid, phosphoric acid, citric acid, formic acid, chromic acid, methanesulfonic acid, ethanesulfonic acid, benzenesulfonic acid, toluenesulfonic acid, folic acid, and salicylic acid.

In some embodiments, the gas compound is an oxide or its derivative, including but not limited to oxygen, nitric oxide, nitrous oxide, nitrogen dioxide, nitrogen dioxide, carbon monoxide, carbon dioxide, sulfur dioxide, ozone, and peroxides.

In some embodiments, the gas compounds are phosphates that may be organic or inorganic, including but not limited to ammonium phosphate, boranophosphate, diammonium phosphate, phosphagen, phosphate, phosphoric acid, phosphotungstic acid, polyphosphate, pyrophosphoric acid, and urea phosphate. In some embodiments, the organophosphates are those used as pesticides, including, but not limited to, Acephate (Orthene), Azinphos-ethyl, Azinphos-methyl (Guthion), Azinphos-methyl oxon, Bromophos-methyl, Carbophenothion (Trithion), Chlorfenvinphos (Supona), Chloropyrifos (Dursban/Lorsban), Chlorpyrifos-methyl, Chlorthiophos, Coumaphos (Co-Ral), Crotoxyphos (Ciodrin), Cyanophos, DEF (Butifos), Demeton (Systox), Demeton-Dialifor (Torak), Diazinon (O Analog), Diazinon (Spectracide), Dichlorvos-DDVP (Vapona), Dicrotophos (Bidrin), Dimethoate (Cygon), Dioxathion (Delnav), Disulfoton (Disyston), Disulfoton Sulfone, Edifenphos, EPN, Ethion (Nialate), Ethoprop (Mocap), Ethyl Parathion, Fenamiphos (Nemacur), Fenitrothion (Sumithion), Fensulfothion (Dasanit), Fenthion (Baytex), Fonofos (Dyfonate), Formothion, Heptenophos, Imidan (Phosmet), Isazophos (Triumph), Isofenphos (Amaze), Leptophos (Phosvel), Malaoxon, Malathion (Celthion), Merphos (Tribufos), Methamidophos (Monitor 4), Methidathion, Methyl Parathion (Metacide), Mevinphos (Phosdrin), Monocrotophos, Naled, Omethoate (Dimethoate O analog), Parathion (Alkron), Paroxon, Phorate (Thimet), Phorate-o, Phorate Sulfone, Phorate Sulfoxide, Phosalone, Phosphamidon (Dimecron), Piperophos, Pirimiphos-ethyl, Pirimiphos-methyl, Profenofos (Curacron), Propetamphos (Safrotin), Pyrazophos (Afgan), Quinalphos, Ronnel (Ectoral) (Fenchlorphos), Sulprofos (Bolstar), Terbufos (Counter), Tetrachlorvinphos (Gardona), Thionazin (Zinophos), and Triazophos (Hostathion). In some embodiments, the organophosphates are nerve agents (e.g., agents of war), including, but not limited to G agents (GD, soman; GB, sarin; and GA, tabun) and the V agents (VX).

II. Reactive Moieties

A wide variety of chemical sensors can be fabricated that will detect trace chemical vapors utilizing the interactions between liquid crystals and the analyte. The physical (e.g., optical and electrical) and the alignment properties of liquid crystal are governed by the intermolecular interactions of its functional moieties where a chemical change in the liquid crystal moiety is likely to alter its properties. Liquid crystal has the ability to influence the rates and energetics of organic reactions due to its integrated molecular arrangements. Incorporating a functional moiety that reacts with the target analyte can affect a change in liquid crystal molecules that will be translated into its observed properties. For example, 3,3'-Dimethylbenzidine is one such moiety that reacts with $NO_2$ to form a chemically altered product.

The present invention provides a method for the detection or differentiation and quantitative measurement of a wide range of chemical vapors, such as oxides of nitrogen, ozone, amines, alcohols, thiols etc. The liquid crystal can be tuned or functionalized by a combination of processes, such as, liquid crystals having reactive organic functional groups (—OH, —C=C—, —C≡C—, —N=N—, —NH$_2$, —COOH etc.), metal-ligand interaction, metal-liquid crystal interaction, metal-ligand-liquid crystal interaction. The choice of a particular liquid crystal composition will be based on the analyte that interacts with LC either by chemical reaction, metal-ligand coordination interaction or dipole-dipole interactions (i.e., by changes in the polarity of the LC environment) that fulfills the requirements: (i) the target vapors should interact strongly with the LC, and (ii) this interaction must be coupled to a change in the LC film supported on the surface.

As an example we proposed here the detection of NO gas using a combination of NO to NO$_2$ oxidation followed by nitrous acid and nitric acid formation in presence of humid environment. The interaction between the analyte and the LC will be dependent on the analyte of interest and the active functional group present in the LC. This particular detection mechanism will involve acid-base, oxidation-reduction, substitution reaction or combinations thereof at the functionalized moiety in the liquid crystal. The interaction of the target analytes with the liquid crystals will manifest as a change in the physical properties of liquid crystals (phase transition, optical birefringence, dielectric anisotropy, magnetic isotropy or even change in the orientation of liquid crystals on a surface) that can be detected using a variety of instruments capable of detecting these physical changes.

In preferred embodiments, the reactive moieties are functional groups available on the liquid crystal that is overlaid on a substrate (described in more detail below). In preferred embodiments, the reactive moieties for nitric oxide detection include amine, aniline, azo and imine functional groups. The present invention is not limited to the use of any particular aniline or amine group(s). Indeed, the use of a variety of substituted aniline compound is contemplated, including, but not limited to, azomethine-type liquid crystals, polyaniline-based moieties and polyimides and combinations thereof. In some embodiments, a substrate is overlaid with a thin film containing the reactive groups. In particularly preferred embodiments, the aniline-like moiety interacts with one or more nitrogen-based compounds of interest (e.g., nitric oxide, nitric acid, or nitrogen dioxide), but does not substantially interact (e.g., display a response of least 95% less or 99% less than that of the targeted nitro-based compound) with an interfering substance such as carbon monoxide, acetone, engine exhaust, wood smoke, cigarette smoke, fabric softeners, diesel fuel, ammonia and facial cosmetics.

A variety of reactive moieties find use in the present invention. In preferred embodiments, the reactive moieties are functional groups available on the liquid crystal that is overlaid on a substrate (described in more detail below). In preferred embodiments, the reactive moieties for nitric oxide include aniline-like groups. The present invention is not limited to the use of any particular aniline-like group. Indeed, the use of a variety of aniline-like groups is contemplated, including, but not limited to, azomethine-type liquid crystals, polyaniline-based moieties and polyimides and combinations thereof. In some embodiments, a substrate is overlaid with a thin film of a solution (containing the previously described aniline-like groups) to provide the reactive groups on the surfaces of the substrate. In particularly preferred embodiments, the aniline-like moiety interacts with one or more nitrogen-based compounds of interest (e.g., nitric oxide, nitric acid, or nitrogen dioxide), but does not substantially interact (e.g., display a response of least 95% less or 99% less than that of the targeted nitro-based compound) with an interfering substance such as carbon monoxide, acetone, engine exhaust, wood smoke, cigarette smoke, fabric softeners, diesel fuel, ammonia and facial cosmetics.

III. Substrates

Substrates that are useful in practicing the present invention can be made of practically any physicochemically stable material. In a preferred embodiment, the substrate material is non-reactive towards the constituents of the mesogenic layer. The substrates can be either rigid or flexible and can be either optically transparent or optically opaque. The substrates can be electrical insulators, conductors or semiconductors. Further, the substrates can be substantially impermeable to liquids, vapors and/or gases or, alternatively, the substrates can be permeable to one or more of these classes of materials. Exemplary substrate materials include, but are not limited to, inorganic crystals, inorganic glasses, inorganic oxides, metals, organic polymers and combinations thereof. In some embodiments, the substrates have micropillared features thereon for the stabilization of the liquid crystal overlay and/or other reagents to the substrate surface or detection regions thereon.

A. Inorganic Crystal and Glasses

In some embodiments of the present invention, inorganic crystals and inorganic glasses are utilized as substrate materials (e.g., LiF, NaF, NaCl, KBr, KI, CaF$_2$, MgF$_2$, HgF$_2$, BN, AsS$_3$, ZnS, Si$_3$N$_4$ and the like). The crystals and glasses can be prepared by art standard techniques (See, e.g., Goodman, C. H. L., Crystal Growth Theory and Techniques, Plenum Press, New York 1974). Alternatively, the crystals can be purchased commercially (e.g., Fischer Scientific). The crystals can be the sole component of the substrate or they can be coated with one or more additional substrate components. Thus, it is within the scope of the present invention to utilize crystals coated with, for example an organic polymer. Additionally, a crystal can constitute a portion of a substrate which contacts another portion of the substrate made of a different material, or a different physical form (e.g., a glass) of the same material. Other useful substrate configurations utilizing inorganic crystals and/or glasses will be apparent to those of skill in the art.

B. Inorganic Oxides

In other embodiments of the present invention, inorganic oxides are utilized as the substrate. Inorganic oxides of use in the present invention include, for example, Cs$_2$O, Mg(OH)$_2$, TiO$_2$, ZrO$_2$, CeO$_2$, Y$_2$O$_3$, Cr$_2$O$_3$, Fe$_2$O$_3$, NiO, ZnO, Al$_2$O$_3$, SiO$_2$ (glass), quartz, In$_2$O$_3$, SO$_2$, PbO$_2$ and the like. The inorganic oxides can be utilized in a variety of physical forms such as films, supported powders, glasses, crystals and the like. A substrate can consist of a single inorganic oxide or a composite of more than one inorganic oxide. For example, a composite of inorganic oxides can have a layered structure (i.e., a second oxide deposited on a first oxide) or two or more oxides can be arranged in a contiguous non-layered structure. In addition, one or more oxides can be admixed as particles of various sizes and deposited on a support such as a glass or metal sheet. Further, a layer of one or more inorganic oxides can be intercalated between two other substrate layers (e.g., metal-oxide-metal, metal-oxide-crystal).

In some embodiments, the substrate is a rigid structure that is impermeable to liquids and gases. In this embodiment, the substrate consists of a glass plate onto which a metal, such as gold is layered by evaporative deposition. In a still further preferred embodiment, the substrate is a glass plate (SiO$_2$) onto which a first metal layer such as titanium or gold has been layered. A layer of a second metal (e.g., gold) is then layered on top of the first metal layer (e.g., titanium).

C. Organic Polymers

In still other embodiments of the present invention, organic polymers are utilized as substrate materials. Organic polymers useful as substrates in the present invention include polymers that are permeable to gases, liquids and molecules in solution. Other useful polymers are those that are impermeable to one or more of these same classes of compounds.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers and phenolic resins (See, Cognard, J. ALIGNMENT OF NEMATIC LIQUID CRYSTALS AND THEIR MIXTURES, in Mol. Cryst. Liq. Cryst. 1:1-74 (1982)). Presently preferred organic polymers include polydimethylsiloxane, polyethylene, polyacrylonitrile, cellulosic materials, polycarbonates and polyvinyl pyridinium.

In some embodiments, the substrate is permeable and it consists of a layer of gold, or gold over titanium, which is deposited on a polymeric membrane, or other material, that is permeable to liquids, vapors and/or gases. The liquids and gases can be pure compounds (e.g., chloroform, carbon monoxide) or they can be compounds which are dispersed in other molecules (e.g., aqueous protein solutions, herbicides in air, alcoholic solutions of small organic molecules). Useful permeable membranes include, but are not limited to, flexible cellulosic materials (e.g., regenerated cellulose dialysis membranes), rigid cellulosic materials (e.g., cellulose ester dialysis membranes), rigid polyvinylidene fluoride membranes, polydimethylsiloxane and track etched polycarbonate membranes.

In a further preferred embodiment, the layer of gold on the permeable membrane is itself permeable. In a still further preferred embodiment, the permeable gold layer has a thickness of about 70 Angstroms or less.

In those embodiments wherein the permeability of the substrate is not a concern and a layer of a metal film is used, the film can be as thick as is necessary for a particular application. For example, if the film is used as an electrode, the film can be thicker than in an embodiment in which it is necessary for the film to be transparent or semi-transparent to light.

Thus, in a preferred embodiment, the film is of a thickness from about 0.01 nanometer to about 1 micrometer. In a further preferred embodiment, the film is of a thickness of from about 5 nanometers to about 100 nanometers. In yet a further preferred embodiment, the film is of a thickness of from about 10 nanometers to about 50 nanometers.

D. Arrays

In some embodiments, the LC composition comprising reactive moieties are arrayed on the substrates using stamping, microcontact printing, or ink-jet printing. In still further embodiments, reactive moieties are spotted onto a suitable substrate. Such spotting can be done by hand with a capillary tube or micropipette, or by an automated spotting apparatus such as those available from Affymetrix and Gilson (See e.g., U.S. Pat. Nos. 5,601,980; 6,242,266; 6,040,193; and 5,700,637; each of which is incorporated herein by reference).

E. Micro-Structured Features

In some embodiments, the substrates utilized in the devices of the present invention comprise one more micro-structured features. In some embodiments, micro-structured features on the substrate augment the spreading of the liquid crystal composition. In still other embodiments, the micro-structured features stabilize the liquid crystal overlay and/or other reagents on the substrate surface or detection regions thereon.

In a paper by Frisk et al (*Lab on a Chip,* 2006, 6, 1504), liquid was dispensed onto a micromachined biosensor substrate that was suspended vertically and remained stably dispersed (and immune to gravitational forces and shock) on that substrate. Following on this result, Sridharamurthy et al (*Smart Mater Struct,* 2008, 17) demonstrated that microstructures could be used to support a film of liquid crystal. In contrast to these systems, in some preferred embodiments, the micro-structured features are made my depositing a polymer on the substrate and etching away areas between the micro-structured features or made from the same material as the substrate. Additionally, in some preferred embodiments, the analyte interacts/reacts with the LC composition rather than competing at the surface of the substrate.

Accordingly, in some embodiments, the micro-features pattern the surface and are selected from the group consisting of a grid, a channel, a plurality of pillars or an array of assay areas or combination thereof. In some embodiments, the micro-features are pillars that project from the surface of the substrates. In some embodiments, the substrates are comprised of glass, silicon, polymer, or a combination thereof. In still further embodiments, the pillars are comprised of the same material as the surface. In other embodiments, the pillars are comprised of a different material than the surface. In preferred embodiments, the substrate is comprised of glass while the pillars are from a polymeric material. The pillars may comprise a shape selected from the group consisting of circular, triangular, square, hexagonal or a combination thereof. The dimension of the pillars could be a variety of heights, widths, and spacing. Indeed, the pillar height may range from 1 micron to 50 microns, the width from 1 micron to 200 microns, and spacing between pillars may range from 1 micron to 200 microns.

IV. Mesogens

Any compound or mixture of compounds that forms a mesogenic layer can be used in conjunction with the present invention. The mesogens can form thermotropic, lyotropic, metallotropic, or cholesteric liquid crystals. The thermotropic, lyotropic, metallotropic, and cholesteric liquid crystals can exist in a number of forms including nematic, isotropic, chiral nematic, smectic, polar smectic, chiral smectic, frustrated phases and discotic phases.

Presently preferred mesogens are displayed in Table 1. In a particularly preferred embodiment, the mesogen is a member selected from the group consisting of 5CB (4-pentyl-4'-cyanobiphenyl), MLC-6812, MLC 12200, MBBA, EBBA, and 8CB (4-cyano-4'octylbiphenyl) and combinations thereof.

The mesogenic layer can be a substantially pure compound, or it can contain other compounds, so called dopants, that enhance or alter characteristics of the mesogen. Thus, in one preferred embodiment, the mesogenic layer further comprises a second compound, for example an alkane, which expands the temperature range over which the nematic and isotropic phases exist. Use of devices having mesogenic layers of this composition allows for detection of the analyte reactive moiety interaction over a greater temperature range.

In some preferred embodiments, the mesogenic layer further comprises a dichroic dye or fluorescent compound. Examples of dichroic dyes and fluorescent compounds TABLE 1
Molecular structure of mesogens suitable for use in Liquid Crystal Assay Devices
| Mesogen | Structure |
|---|---|
| Anisaldazine | 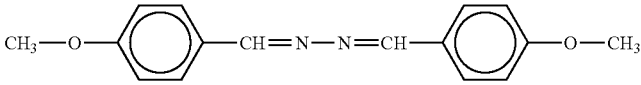 |
| NCB | 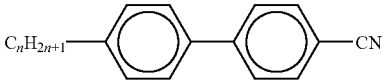 |
| CBOOA | 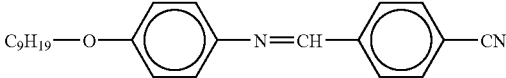 |
| Comp A | 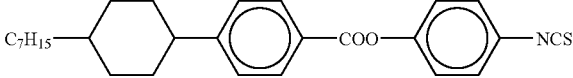 |
| Comp B | 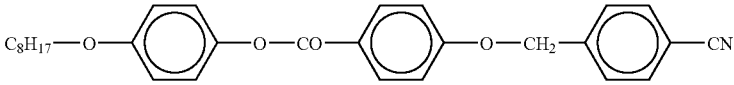 |
| $DB_7NO_2$ | 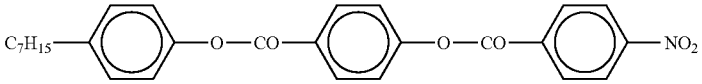 |
| DOBAMBC | 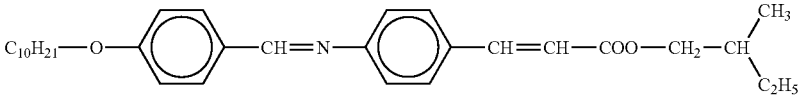 |
| $nOm$<br>n = 1, m = 4: MBBA<br>n = 2, m = 4: EBBA | 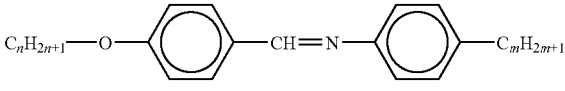 |
| $nOBA$<br>n = 8: OOBA<br>n = 9: NOBA | 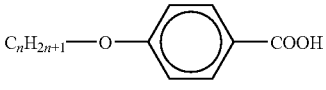 |
| $nmOBC$ | 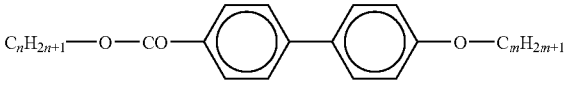 |
| $nOCB$ | 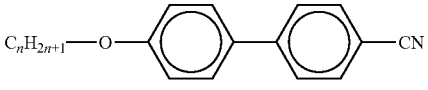 |
| $nOSI$ | 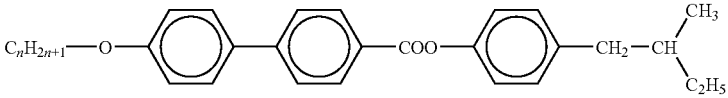 |
| 98P | 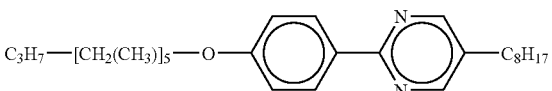 |
| PAA | 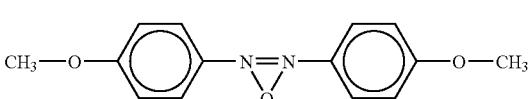 |
| PYP906 | 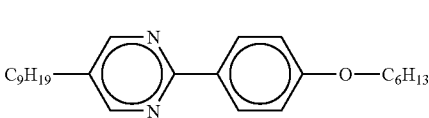 |

TABLE 1-continued

Molecular structure of mesogens suitable for use in Liquid Crystal Assay Devices

| Mesogen | Structure |
|---|---|
| $\overline{n}Sm$ | $C_nH_{2n+1}$—O—⟨⟩—CO—S—⟨⟩—$C_mH_{2m+1}$ | useful in the present invention include, but are not limited to, azobenzene, BTBP, polyazo compounds, anthraquinone, perylene dyes, and the like. In particularly preferred embodiments, a dichroic dye or fluorescent compound is selected that complements the orientation dependence of the liquid crystal so that polarized light is not required to read the assay. In some preferred embodiments, if the absorbance of the liquid crystal is in the visible range, then phase changes can be observed using ambient light without crossed polars. In other preferred embodiments, the dichroic dye or fluorescent compound is used in combination with a fluorimeter and the changes in fluorescence are used to detect changes in phase transition of the liquid crystal.

V. Detection of Gas Phase Compounds

The present invention provides methods and devices for the detection of gas phase compounds in a sample. The device of the present invention can be of any configuration which allows for the contact of a mesogenic layer providing reactive moieties and supported by a substrate. The only limitations on size and shape are those that arise from the situation in which the device is used or the purpose for which it is intended. In some embodiments, the devices comprise a single substrate that is open to the environment on one surface. The device can be planar or non-planar. The device can be cylindrical in shape and in a linear or coiled format, and with one or two ends of the cylinder open to the environment. Furthermore, it is within the scope of the present invention to use any number of polarizers, lenses, filters, lights, and the like to practice the present invention. The present invention is not limited to any particular mechanism of action. Indeed, an understanding of the mechanism of action is not necessary to practice the present invention. Nevertheless, it is contemplated that the mesogens forming the liquid crystal of the devices of the present invention provide reactive moieties that have an affinity for the targeted compound. This affinity causes a phase transition of the liquid crystal in the presence of the target. Particular mesogens will transition from a higher order to a lower order following interaction with different molecules. The devices of the present invention are designed so that when gas phase compounds are present in a sample, the gas can enter detection regions of the device where mesogens are arrayed and cause a change in the phase order of the mesogen by interacting with the reactive moiety on the mesogen. This phase transition may be from one phase selected from the group consisting of an isotropic phase, a nematic phase, and a smectic phase to another phase selected from the group consisting of an isotopic phase, a nematic phase and a smectic phase. The phase transition induces a change in the liquid crystal (i.e., a nematic region as opposed to an isotropic region) that can be detected in a variety of ways.

In some embodiments, the present invention provides substrates overlaid with mesogens into which the gas phase compound diffuses leading to a phase transition of the mesogen. In other embodiments, the gas phase compound interacts directly with the reactive moiety of the mesogen to induce the phase change of the mesogen. In still other embodiments, the gas phase compound diffuses into a mesogen composition containing a dopant and interacts with a reactive moiety on the dopant leading to a phase transition of the mesogen.

Accordingly, in some embodiments, the present invention provides substrates comprising at least one detection region comprising a mesogen composition comprising a reactive moiety (e.g., an aniline-like group) that binds to or otherwise interacts with gas phase compound. In preferred embodiments, the detection regions are discrete and created by arraying at least one reactive moiety on the surface of the substrate. In preferred embodiments, the reactive moiety is contained in bulk in a coiled cylindrical substrate as described in detail above. In some embodiments, a plurality of mesogens with various reactive moieties are arrayed on the surface of the substrate so that multiplexed assays for a variety of gas phase compounds can be conducted or so that different interactions with a variety of reactive moieties can be used as a signature for a particular gas phase compound. In some preferred embodiments, a liquid handler is used to deposit the mesogen composition in the detection region.

In some embodiments, a second substrate is provided which is configured opposite the first substrate so that a cell is formed. In some embodiments, the second substrate is also arrayed with one or mesogen compositions comprising a reactive moiety, while in other embodiments, the second substrate is free of reactive moieties. In some preferred embodiments, the mesogen compositions comprising a reactive moiety are arrayed on the first and second substrates so that when the first and second substrates are placed opposite each other the arrays match to form discrete detection regions.

In some embodiments, the cell that is formed by the first and second substrates includes a space between the first and second substrates. In some embodiments, the space is formed by placing a spacer between the first and second substrates. In some embodiments, the space is then filled with the desired liquid crystal. In still other embodiments, the substrates are arranged so that a sample can interact with or enter into the detection regions. In some embodiments, the substrates are fixed (e.g., permanently or removably) to one another. The present invention is not limited to any particular mode of fixation. Indeed, a variety of modes of fixation are contemplated. In some embodiments, the substrates are fixed to one another via adhesive tape. In preferred embodiments, the adhesive tape is 8141 pressure sensitive adhesive (3M, Minneapolis, Minn.). In other embodiments, the substrates are fixed to one another via a UV curable adhesive. In some preferred embodiments, the UV curable adhesive is PHOTOLEC® A704 or A720 (Sekisui, Hong Kong). In some embodiments, glass spacer rods are utilized with the UV curable adhesive to provide spacing between the two substrates. In some embodiments, the glass spacer rods range from about 5 µM to about 100 µM, preferably about 25 µM. It has been found that UV curable adhesives are preferable as in some instances the adhesive tape reacts with the liquid crystal.

In further embodiments, the substrates are arranged in a housing. The housing can comprise any suitable material, and is preferably made of polymeric material, for example, a plastic. In preferred embodiments, the housing is sealed to the environment except for an opening adjacent to the detection region or regions. The opening preferably allows diffusion of air to the detection region. In some embodiments, the opening allows introduction of a liquid sample wherein gas emitted from a constituent in the sample impinges on the substrates and can be interrogated. In some embodiments, the opening is covered with a filter material that allows diffusion of air to the detection region, but does not allow entry of particulate matter such as dust, dirt, liquid, and insects into the detection region. In some embodiments, the filter is an aerosol filter that substantially prevents the introduction of aerosols into the detection region, but allows an analyte such a nitrogen compound in vapor form to enter the detection region. In still more preferred embodiments, the devices comprise two or more filters positioned so as to allow air-exchange though the device, and in particular, through the detection region. For example, the filters can be arranged at either end of the detection region. In further embodiments, the housing is moveable between an exposure mode and a reading mode. In the exposure mode, the detection regions are exposed to the environment, while in the reading mode, exposure to the environment is substantially or completely eliminated. It is envisioned that after the device has been exposed to the environment, the housing can be moved to the reading mode to prevent further exposure to the environment prior to readout.

In still further embodiments, the devices of the present invention comprise a unique identifier. In some embodiments, the unique identifier is a bar code. In other embodiments, the unique identifier is an RFID chip. It is contemplated that the unique identifier can provide information such as a serial number, user identification, source identification, and the like.

In use, the device is placed in an area where the gas phase compounds are suspected of being present. The device is allowed to remain in place for a period of time (the exposure period, e.g., from 1 day to four weeks). In a preferred use, the device is brought in contact with a person's mouth and used to collect and analyze exhaled breath as a personal breath monitor. The device is allowed to remain in place for the duration of 1-2 exhalations (the exposure period, e.g., from 10 to 30 seconds).

In other uses, a liquid sample that is biological or pharmaceutical in nature and suspected of containing bacteria is introduced into the device. The sample is allowed to incubate for a period of time (the exposure period, e.g., from 15 minutes to 4 days). In a preferred use, the device receives a liquid sample and is incubated at 37C for 1 hour with shaking to permit replication of bacteria that leads to release of metabolic gases.

Following the exposure period, the cell is assayed for whether a change in the liquid crystal phase has occurred over one or more of the detection regions. Although many changes in the mesogenic layer can be detected by visual observation under ambient light, any means for detecting the change in the mesogenic layer can be incorporated into, or used in conjunction with, the device. Thus, it is within the scope of the present invention to use lights, microscopes, spectrometry, electrical techniques and the like to aid in the detection of a change in the mesogenic layer. In some embodiments, the presence of gas phase compounds is detected by a change in the color and texture of the liquid crystal.

Accordingly, in those embodiments utilizing light in the visible region of the spectrum, the light can be used to simply illuminate details of the mesogenic layer. Alternatively, the light can be passed through the mesogenic layer and the amount of light transmitted, absorbed or reflected can be measured. The device can utilize a backlighting device such as that described in U.S. Pat. No. 5,739,879, incorporated herein by reference. Light in the ultraviolet and infrared regions is also of use in the present invention. In other embodiments, the device, and in particular the detection region, is illuminated with monochromatic light source (e.g., 660 nm LEDs). In some embodiments, the cell is placed in between cross-polar lenses and light is passed though the lenses and the cell. In still other embodiments, the detection region is masked off from the rest of the device by a template or mask that is placed over the device.

The devices of the present invention are useful for measuring cumulative exposure to gas phase compounds. In some embodiments, cumulative exposure is assayed by determining the advancement of a wavefront in the detection region. It is contemplated that the wavefront advances from opening associated with the detection region. The distance of advancement correlates to the degree of exposure to gas phase compounds and is thus quantitative. In particular, it is contemplated that the rate of progress of the wavefront into the detection region depends on the concentration of gas phase compound to which the device is exposed. In preferred embodiments, the front movement in millimeters is plotted against elapsed time in hours. The resulting plot obeys a linear fit (preferably with a coefficient of correlation of greater than 0.95) characteristic the concentration of gas phase compound in the sample (e.g., local atmosphere). In some preferred embodiments, wavefront advancement is measured capturing a digital image of the detection region and determining the area and length of the wavefront from the opening in pixels. In some preferred embodiments, the image is analyzed with a program such as Scion Image (NIH Freeware). The pixels can then be converted into millimeters if necessary. In other embodiments, the image is analyzed by converting the image with a % white command so that the area in which the liquid crystal has been disrupted by the gas phase compound appears white. The degree of advancement of the wavefront can be determined by measuring pixel intensity and determining where image drop-off from high intensity (white) to low intensity (black).

The devices of the present invention can also be used to identify particular gas phase compounds. In some embodiments, the detection region of the device comprises an array of at least two different mesogens. The pattern of response to the at least two different mesogens can be used to identify particular compounds.

A. Reflection Based Probing

In some embodiments, the devices of the present invention form a Fabry-Perot filter. The present invention is not limited to a particular mechanism. Indeed, an understanding of the mechanism of the present invention is not needed to practice the invention. Nevertheless, when electromagnetic radiation propagates through an interface between two dielectric media it undergoes reflection at the interface. If a dielectric material is sandwiched between two highly reflecting mirrors forming a cavity, multiple reflection of radiation occurs in the cavity. For a given thickness and the dielectric properties of the cavity, the reflected electromagnetic radiation interferes constructively and shows a maximum at a particular wavelength. The wavelength at which the reflected radiation shows peak intensity depends on the thickness of cavity and the dielectric property of the cavity. When the refractive index of the cavity changes, the wavelength at which the maximum reflection occurs also changes. If the mirrors are functionalized with receptors targeted to the specific analyte, binding of the target induces an orientational transition of the LC and hence a change in the dielectric property of the cavity. This change in the dielectric constant results in a shift in the wavelength at which the reflected intensity is maximal.

In some embodiments, the Fabry-Perot filter devices comprise a first surface (e.g., an interior surface) displaying one or more mesogen compositions comprising a reactive moiety. In some embodiments, the surface is reflective. In preferred embodiments, the first surface is gold. In some preferred embodiments, the gold is deposited on a supporting substrate, such as glass or silicon. Other suitable substrates are described in more detail above. In further preferred embodiments, the devices comprise a second surface coated in a reflective material, preferably gold. In some embodiments, the second surface also displays one or more mesogen compositions comprising a reactive moiety. In some embodiments, the first and second surfaces are configured opposite one another to form a chamber there between. Preferably, the chamber is fillable with a liquid crystal. Preferred mesogens forming the liquid crystal are listed above and include, but are not limited to, MLC-6812, MLC 12200, MBBA, EBBA, 5CB (4-n-pentyl-4'-cyanobiphenyl), and 8CB (4-cyano-4'octylbiphenyl).

In still further embodiments, at least one mesogen composition comprising a reactive moiety is deposited or otherwise interacts with the first or second surfaces. The present invention is not limited to any particular reactive moiety. Indeed, a variety of reactive moieties may be utilized, including, but not limited to, an organic functional group selected from the group consisting of amines, carboxylic acids, drugs, chelating agents, crown ethers, cyclodextrins or a combination thereof, a biomolecule selected from the group consisting of a protein, antigen binding protein such as a monoclonal antibody, polyclonal antibody, chimeric antibody, humanized antibody, Fab fragment, single chain antibody, etc., peptide, nucleic acid (e.g., single nucleotides or nucleosides, oligonucleotides, polynucleotides and single- and higher-stranded nucleic acids) or combinations thereof.

The present invention is not limited to any particular substrate shape. Indeed, a variety of substrate shapes are contemplated, including, but not limited to, discs, cylinders, and spheres. Disc shaped devices are preferably configured as described above, with a single planar surface that is overlaid with a liquid crystal. In preferred embodiments, the discs have a diameter of between about 0.1 mm to 10 cm, preferably about 1 mm to about 100 mm. In some preferred embodiments, highly reflecting mirrors are prepared by depositing ~500 nanometer thick gold films on clean glass slides (or plastic films) using electron beam evaporator. In further preferred embodiments, these gold mirrors are layered with mesogens that provide a reactive moiety. In further embodiments, glass fiber rods with approximately a 25 micron diameter mixed in isopropanol are sprayed uniformly over one of the functionalized mirrors. These rods act as spaces defining the thickness of the dielectric cavity. An optical cell is fabricated forming a cavity between two reflecting mirrors. In some embodiments, the mirrors are glued together using UV curable adhesives. The cavity is then filled with the liquid crystal, such as 4-n-pentyl-4'-cyanobiphenyl (5CB). The present invention is not limited to a particular mechanism of action. Indeed an understanding of the mechanism of action is not necessary to practice the present invention. Nevertheless, without exposure to the target analyte, the liquid crystals assume one preferred phase (for example nematic). In some embodiments, the mirror assembly is placed in the path of the light in a spectrometer. For the optimized thickness, a peak appears in the transmitted intensity at a particular wavelength determined by the ordinary refractive index of the LC materials. In some embodiments, upon exposure to an analyte (such as nitric acid or nitrogen dioxide), the liquid crystal undergoes a phase transition (for example to isotropic). In some preferred embodiments, the device is placed in a light path. A peak appears at a wavelength that corresponds to the average refractive of the nematic phase. The shift in the peak position of the transmission spectrum indicates a change in the refractive index of the cavity caused by the phase transition of the liquid crystal that is induced by interaction of the analyte with the reactive moieties of the mesogen on the surface.

In other preferred embodiments, hollow polymer cylinders (about 100 to 1000 microns in diameter, and preferably about 500 micron in diameter; about 1 mm to 1 cm in length, preferably about 5 mm in length) are first coated with a reflective material such as gold. Preferably the coating is from about 50 to about 1000 nm in thickness, and most preferably about 500 nm thick. A spacer is then formed on the cylinder. In some embodiments, the spacer is from about 50 to about 200 microns in thickness, preferably about 25 microns. In some preferred embodiments, the spacer comprises glass fiber rods with desired diameter preferably 25 microns (such as from EM Industries) or plastic micropearls (spheres) of desired diameter preferably 25 micron (such as from Sekesui Chemicals, Hong Kong). In some preferred embodiments, these spacers are mixed in isopropyl alcohol and then sprayed on to the cylinders. A ~25 micron sacrificial layer of photoresist is then coated to these cylinders. Examples of useful photoresist layers include, but are not limited to SU8 2010 from Michochem. Another thin nanoporous layer of gold is deposited on top of the sacrificial layer. The gold film with nanopores is strongly reflecting but allows small molecules to penetrate through it. The sacrificial layer is then dissolved in acetone. The spacers in between two gold surfaces act as supporting struts. These hollow cylinders are then filled with a liquid crystal. In still further embodiments, the first surface is spherical and a second surface and chamber are formed as described for the cylinder embodiments.

In other embodiments, the devices of the present invention form a rugate filter. Again, the present invention is not limited to a particular mechanism. Indeed, an understanding of the mechanism of the present invention is not needed to practice the invention. Nevertheless, as the electromagnetic radiation propagates through a number of interfaces between dielectric layers, multiple reflections occur at each interface and a portion of the radiation is transmitted and a portion of it is reflected. If the dielectric constant of the medium exhibits sinusoidal variation, then the reflected intensity shows a peak in the reflected intensity at a wavelength that depends on the average dielectric constant and the amplitude of sinusoidal variation of dielectric constant. The position of the reflected peak in the electromagnetic spectrum shifts as the average refractive index of the sinusoidal variation changes. Accordingly, in some embodiments, a sinusoidal variation in the dielectric property is created by fabricating porous silicon with sinusoidal porosity gradient along the depth. See, e.g., Li et al., Science 299:2045-47 (2003); Seals et al., J. Applied. Phys. 91(4):2519-23 (2002); Schmedake et al., Adv. Mater. 14(18):1270-72 (2002); Link and Sailor, Proc. Nat'l. Acad. Sci. USA 100(19):10607-10 (2003), all of which are incorporated herein by reference in their entirety. When the pores are filled with LCs, the LCs take on a specific phase. Upon exposure to the target analyte the LC undergoes a phase transition, which induces a change in the dielectric constant of the pores resulting in a shift in the position of the peak.

The present invention is not limited to the use of any particular type of silicon substrate. In some embodiments, the silicon substrate is p-type, boron doped silicon wafer with about a 1 mOhm cm resistivity and polished on 100 face. The silicon substrate is preferably ultrasonicated in isopropanol and then rinsed with water. In some embodiments, the silicon wafers are etched using an anodization-etching process with a mixture of 48% hydrofluoric acid and absolute ethanol (1:3 by volume) in a Teflon cell using a sinusoidally modulated current density to generate a sinusoidal variation in the porosity gradient. In further embodiments, the amplitude, period, and duration of the sinusoidal current density is adjusted to achieve the optimum porous size and distribution. It will be recognized that these parameters can be varied and optimized for the detection of different analytes. In still further embodiments, the current density is then ramped up so that a freestanding film of the porous silicon is detached from the substrate.

In still further embodiments, devices such as those described above are irradiated with electromagnetic radiation from the radio frequency region, including, but not limited to, frequencies between 1 KHz and 10 THz, and including the VLF, LF, MF, HF, VHF, UHF, SHF and EHF regions of the radio spectrum. Studies have demonstrated that analysis of the reflection and/or transmission spectra of RF radiation can be used to identify analytes. See, e.g., U.S. Pat. Appl. 2004086929, Choi et al., Int'l. J. High Speed Electronics and Systems 13(4):937-950 (2003); van der Weide, Springer Series in Optical Sciences (2003), 85:317-334 (2003), all of which are incorporated herein by reference. In some preferred embodiments of the invention, a change in phase of a liquid crystal gives rise to a change in the reflection or transmission spectra of RF radiation. In further preferred embodiments of the invention, the frequency of the radiation is in the 0.1-10 THz range. Methods known to those skilled in the art are used to analyze the radiation returned to a detector following interaction with the liquid crystal.

B. Photoluminescence

In some embodiments, a liquid crystal phase transition is detected by photoluminescence. The present invention is not limited to a particular mechanism of action. Indeed, an understanding of the mechanism of action is not necessary to understand the present invention. Nevertheless, when silicon with nanometer scale porous structure is exposed to electromagnetic radiation at short wavelength, typically in the ultraviolet region, electron-hole pairs are created. These excess carriers subsequently recombine radiating electromagnetic radiation. As the characteristic size of the structures in the porous silicon decreases to the nanometer scales, the band gap of the silicon nanostructures progressively widens. The recombination of these quantum confined carriers (electron-hole pair) in the wide band gap causes emission of electromagnetic radiation in the visible region. The wavelength of the emitted light depends on the dielectric constant of the materials filling the pores, besides the detailed structure of the pores themselves. When the surfaces of the pores are filled with the liquid crystal, the liquid crystal takes on a preferred phase (nematic). The porous silicon then emits light at a wavelength that corresponds to the radial distribution of the liquid crystal molecules. When the target analyte binds to the reactive moieties on the mesogens filling the pores, liquid crystal undergoes a phase transition to isotropic causing a change in the dielectric constant. This results in a change in the position of the peak. It will be recognized that the present invention is not limited to any particular type of change in liquid crystal phase and that the described change from nematic to isotropic is exemplary. Other changes are also contemplated, including, for example, from smectic to nematic or changes in the amount of twist, where, for example, cholesteric liquid crystals are utilized.

In some embodiments, porous silicon substrates are fabricated and functionalized as described above. In further embodiments, the porous silicon is illuminated by a UV light. The exact wavelength of the UV light depends on the actual porous size, porous size distribution and the refractive index of the liquid crystal material. The photoluminescence of the porous silicon is measured using UV-Visible spectrophotometer. The spectrum shows a peak at a wavelength corresponding to the phase of the liquid crystal. In some preferred embodiments, the porous silicon is now exposed to the target analyte in a closed chamber. The present invention is not limited to any particular mechanism of action. Indeed, an understanding of the mechanism of action is not necessary to understand the present invention. Nevertheless, as the target analyte binds to the reactive moiety provided by the mesogen on the surface of the pores the LC undergoes a phase transition. It is contemplated that the change in the phase of the liquid crystal corresponds to a change in the spectrum of radiation emitted by the porous silicon.

C. Fluorescence Based Detection

In other embodiments, detection is accomplished using a fluorescent reporter system. The present invention is not limited to any particular mechanism of action. Indeed, an understanding of the mechanism of action is not necessary to understand the present invention. Nevertheless, certain compounds such as 4-(4-dihexadecylsminostyryl)-N-methylpyridinium iodide (DIA), 1,3,5,7,8-pentamethyl-2,6,-di-t-butylpyrromethane-difluoreborate PM-597, 4-(dicynaomethylene)-2-methyl-6-(4-dimethylamino styryl)-4H-pyran (DCM), europium (III) thenoyltrifluoroacetonate trihydrate [Eu(TTA)$_3$.H$_2$O] etc., when dissolved in liquid crystal emit visible light upon exposure to UV light. The intensity and the wavelength of the emitted light depend on the orientation of the dye molecules with respect to liquid crystal phase. If the dye molecules are immobilized on to the surface in a fixed orientation with respect to the surface and the liquid crystal undergoes phase transition, the characteristics of the emitted radiation changes. When analyte binds to the receptor, the liquid crystal undergoes phase transition, the wavelength of the emitted light changes.

Accordingly, in some embodiments, a thin gold film is deposited on a substrate (preferably a UV transparent quartz substrate or plastic film) using an electron beam evaporator. The gold surface assembled into a liquid crystal assay device using small glass spacer rods as described above. The device is then filled with a liquid crystal that provides a reactive moiety. The present invention is not limited to any particular mechanism of action. Indeed, an understanding of the mechanism of action is not necessary to understand the present invention. Nevertheless, without exposure to the target analyte, the liquid crystal takes on one preferred phase, for example, nematic. In preferred embodiments, the optical cell is irradiated with UV light, which in some preferred embodiments is provided by a laser. In the absence of the analyte the fluorescent molecules emit visible light at a wavelength that corresponds to the nematic phase of liquid crystals. When the device is exposed to an analyte (such as nitric oxide or nitrogen dioxide) the liquid crystal undergoes phase transition to, for example, an isotropic phase. The shift in the peak position of the fluorescence spectrum (change in the color of the emitted light) indicates a change in the dielectric environment of the fluorescent molecules on the surface. This change is caused by the phase transition of the liquid induced by binding of the analyte to the reactive moiety on the mesogen.

In other embodiments of the invention, fluorescent dye molecules such as Acridine Orange Base, Rhodamine 6G, perchlorate, 5-decyl-4,4-difluoro-4-bora-3a,4a-diaza-s-indacene-3-propionic acid, Nile Red, N,N' Bis(2,5-di-tert-butylphenyl)-3,4,9,10-perylenedicarboximide, etc., are dissolved into the liquid crystal forming a guest-host system. The present invention is not limited to any particular mechanism of action. Indeed, an understanding of the mechanism of action is not necessary to understand the present invention. Nevertheless, the orientation of the dye molecule, in general, is dependent on the phase of the LC in the LC cell. When a beam of light (typically in the visible region) with its polarization parallel to the transition dipole moment of the dye, is passed through the guest host system, it gets absorbed by the dye molecule. The dye molecules then radiate visible light at a different wavelength. However, if the incident light has its polarization perpendicular to the transition dipole moment of the dye molecule it is not absorbed and the dye molecule do not emit any radiation. Therefore, in the absence of the target analyte, when the guest-host system is interrogated by a polarized light corresponding to the excitation wavelength of the dye used, the light coming from the system is composed of the excitation wavelength. If the analyte is present in the ambient, it interacts with the functionalized surface and the liquid crystal undergoes phase transition from the nematic to the isotropic phase. This causes a rotation of the transition moment of the dye molecule parallel to the polarization direction of the excitation beam. The dye molecules then absorb the incident wavelength and emit light at different wavelength. Thus, by probing liquid crystal-dye mixture using polarized light propagating perpendicular to the cell surface, the presence of the analyte in the environment can be probed. The liquid crystal assay device cell is fabricated as described above except that it is filled with liquid crystal-dye mixture. For the interrogation, the polarization can be integrated on the liquid crystal cell or can be probed by sending polarized light.

In still further embodiments, the fluorescent properties of quantum dots are utilized for detection of analytes. The present invention is not limited to any particular mechanism of action. Indeed, an understanding of the mechanism of action is not necessary to understand the present invention. Nevertheless, some semiconductor quantum dots with nanometer size emit visible light when exposed to UV radiation. Due to the quantum confinement the electron-hole pairs trapped at the surface have a large a large band gap. Because of this large band gap, these semiconductor quantum dots absorb light in the UV region. The wavelength of light emitted by these fluorescence particles depends, besides their size, on properties of the surrounding medium, such as but not limited to, the dielectric constant of the surrounding medium. In some preferred embodiments, these quantum dots are functionalized with the receptors targeted for the analyte so that a liquid crystal in contact with them assumes an orientation perpendicular to the surface of the quantum dots. Upon irradiation from a UV light source, the fluorescent spectrum shows a peak at a particular wavelength. When these dots are exposed to the analyte, the liquid crystal undergoes phase transition, which causes a shift in the peak position.

The present invention is not limited to the use of any particular type of quantum dot. In some preferred embodiments, cadmium selenide quantum dots with thin zinc sulfide and polymer coatings are functionalized with a carboxylic acid terminated organic layer (for example 11-mercaptoundecanoic acid) and then treated to display a reactive moiety as described above (e.g., aniline-like groups). In some preferred embodiments, the quantum dots are dispersed in a liquid crystal (e.g., 5CB). The functionalized quantum dots influence the phase of the liquid crystals (nematic). In further preferred embodiments, a liquid crystal assay device is fabricated by forming a cavity (preferably 5 to 100 microns, most preferably about 25 microns) between two untreated UV transparent quartz substrates. The cavity between the substrates is filled with the mixture of functionalized quantum dots and liquid crystal. In still further preferred embodiments, the optical cell is exposed to an analyte (such as nitric oxide or nitrogen dioxide) and then probed with a UV light source, such as a laser. When the analyte binds to the receptors on the quantum dots, the liquid crystal undergoes a phase transition to isotropic, disrupting the quantum dots and thereby affecting the color of light emitted by them.

D. Electrical Detection

In some embodiments the change in physical properties of LC will be detected by measurement in change in the dielectric constant of liquid crystals as a result of interaction of the analytes with LCs.

VI. Breath Monitors

In some embodiments, the present invention provides breath monitors for the detection of exhaled breath components. In preferred embodiments, the breath monitors comprise one or more substrates as described in detail above. In further embodiments, the breath monitors comprise a substrate, breathing tube, electronic components for detecting, measuring and reporting the signal on the substrate, and a housing unit. In some embodiments, the housing protects the electronics, provides a chamber into which the substrate is inserted and provides a fitting into which the exhalation tube is engaged. In some embodiments, the substrate and breathing tube are disposable while the housing containing the electronic components is reusable. In some embodiments, the substrates are provided in quantity for insertion into the housing. In still other embodiments, the breath monitor is provided with instructions for using the disposable substrates and exhalation tube in conjunction with the monitor for the direct or indirect detection of at least one breath component. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510 (k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); C (degrees Centigrade); U (units), mU (milliunits); min. (minutes); sec. (seconds).

Example 1

Screening of LCs for Ability to Detect Nitric Acid Vapor

This example describes the identification of liquid crystals that can be used for detection of nitric acid vapor. The screen was performed by using a single substrate that contained a 3×3 array of micropillar features to aid in spreading and maintaining a thin film of liquid crystals, as shown in FIG. 2. The substrate was treated with titanium and gold. The substrates were prepared by depositing ultrathin (optically transparent) gold films onto glass substrate by electron beam deposition. Uniformly coated chips (100 Angstrom gold on a 20 Angstrom titanium adhesion layer) with micropillar features were spotted with ~0.6 μl of 9 different liquid crystal candidates (FIG. 1). The sensor chip was placed into a petri dish and a 110 μl droplet of 70% aqueous solution of nitric acid ($HNO_3$) was deposited proximal to the chip inside the dish. The dish was covered with a lid and the edges were sealed by wrapping with parafilm. This exposure chamber was sandwiched between crossed-polarizing filters and placed between a light box and a digital camera in order to observe the behavior of the LC. In this set-up, the air inside the petri dish was essentially equivalent to that of room air. After time, the liquid droplet of nitric acid began to vaporize and thus changed the composition of the air inside the petri dish. Images of the sensor arrays were captured using a Qimaging digital camera at various time intervals ranging from 0 minutes to 1 hour 45 minutes. Representative images of the 3×3 arrayed sensors are shown in FIG. 2. The results indicate that 5CB (spot 1), MLC 6812-100 (spot 5) and MLC-12200-100 (spot 7) undergo phase change upon exposure to nitric acid vapor. This is evident by the change in optical appearance of the LC spots. At time 0, in the absence of $HNO_3$ vapor, all of the areas supporting LC films appear bright under crossed polarizers. In this configuration, the gold coated substrate aligns the nematic LCs in a random planar orientation which permits the passage of light through the polarizers. However, in the presence of HNO3 three of the LCs interact with the gas vapor and a phase transition of the LC to isotropic liquid is elicited. The outcome is that polarized light is no longer able to pass and the sensor appears dark in the spots supporting 5CB, MLC-12200, and MLC-6812-100.

Example 2

Specificity of LCs for Detection of Nitric Acid Vapor

This example describes the specificity of 3 LCs for detection of nitric acid vapors. The screen was performed by using a single substrate that contained a 3×3 array of micropillar features, as shown in FIG. 4. The substrate was treated with titanium and gold. The substrates were prepared by depositing ultrathin (optically transparent) gold films onto a glass substrate by electron beam deposition. Uniformly coated chips (100 Angstrom gold on a 15 Angstrom titanium adhesion layer) with micropillar features were spotted with ~0.6 μl of 9 different liquid crystal candidates (FIG. 3). The sensor chip was placed into a petri dish and a 110 μl aqueous solution of either nitric acid ($HNO_3$, 70%), hydrochloric acid (HCl, 37%) or sulfuric acid ($H_2SO_4$, 70%) was deposited proximal to the chip inside the dish. The dish was covered with a lid and the edges were sealed by wrapping with parafilm. This exposure chamber was sandwiched between crossed-polarizing filters and placed on a between a light source and a digital camera in order to observe the behavior of the LC. In this set-up, the air inside the petri dish was essentially equivalent to that of room air. After time, the acid solutions began to vaporize and thus changed the composition of the air inside the petri dish. Images of the sensor arrays were captured using a Qimaging digital camera at various time intervals ranging from 0 to 20 minutes. Representative images of the 3×3 arrayed sensors are shown in FIG. 4. The results indicate that none of the LCs react in the presence of HCl or $H_2SO_4$ while the 5CB (spot 1), MLC 6812-100 (spot 3) and MLC-12200-100 (spot 5) did undergo phase change upon exposure to $HNO_3$ vapor. Additionally, the sensors that did not react in the presence of HCl and H2SO4 where later exposed to HNO3 vapor and showed phase changes on spots 1, 3, and 5 (5CB, MLC 6812-100 and MLC-12200-100, respectively). Also, identical sensor substrates were exposed to water vapor by placing the LC-coated substrates in the proximity of a droplet of water in a closed petri dish as described above. Among the nine liquid crystals tested, there was no change observed in the appearance of any of the spots. These data support the conclusion that the LCs that undergo phase change in the presence of $HNO_3$ yet do not respond to other acids tested or water used as a solvent for acids in this study, i.e., indicating specificity.

Example 3

Detection of Nitrogen Dioxide Using LC-Based Sensors

Figure 5:
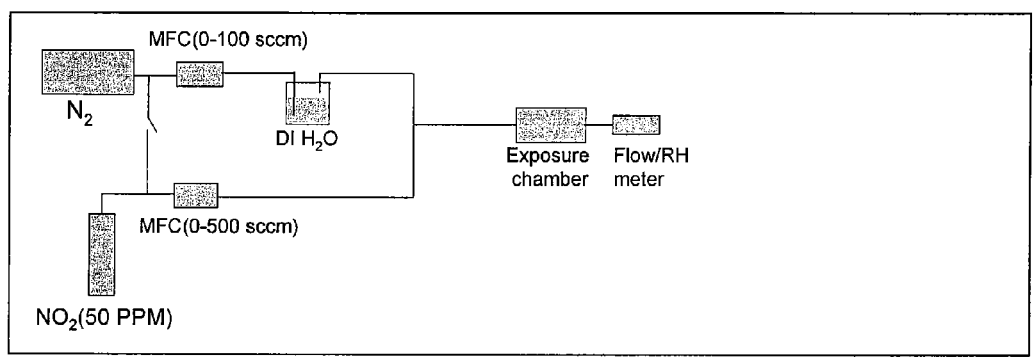
FIG. 5 is a schematic of the experimental setup for detection of nitrogen dioxide using LC-based sensors.
Figure 6:
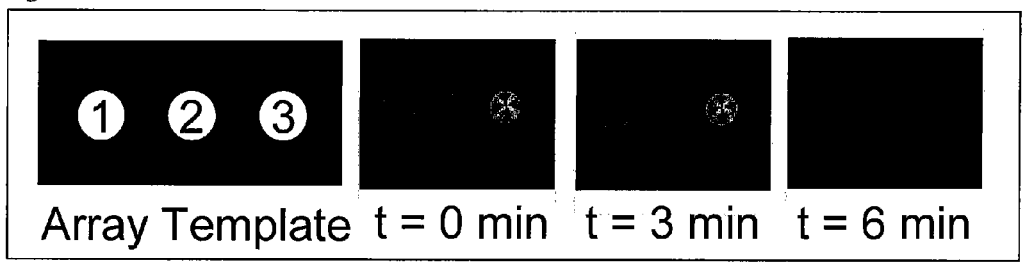
FIG. 6 provides a template and images of sensor with a 1×3 array of 3 LCs following exposure to 5 ppm of nitrogen dioxide that had been converted to nitric acid.

This example describes the conversion of nitrogen dioxide to nitric acid vapor and the subsequent detection by liquid crystals. Nitric acid vapor was generated by mixing nitrogen dioxide ($NO_2$) gas at 50 ppm in nitrogen with moist nitrogen ($N_2$) generated by bubbling through water. The rate of flow of each gas, i.e., $NO_2$ and $N_2$ (bubbled through water), was adjusted using mass flow controllers (0-100 sccm and 0-500 sccm) to achieve desired concentrations and then the gases were mixed together. The flow of the nitrogen dioxide and nitrogen bubbled through water was adjusted so that the total flow was 200 sccm. The relative humidity of the nitrogen bubbled through water was ~96% and reduced to ~80% after mixing with nitrogen dioxide. A diagram of the gas generation system and exposure set-up is provided in FIG. 5. The sensor consisted of a 1×3 array of three different liquid crystals (5CB, MLC 6812-000 and MLC 12200-100) that were spotted in a small volume onto substrates that provided micropillar features (10 μm diameter, 10 μm spacing, and 5 μm tall). The sensor was placed at the center of a small exposure chamber that was placed between crossed polarizers. The exposure chamber and polarizers were positioned between a light source and a digital camera. Digital images were captured using a Qimaging camera at regular intervals to monitor the change in appearance of the LC film as it was exposed to the analytes. For a negative control, the nitrogen dioxide gas was replaced by nitrogen gas flowing through the same mass flow controller. The sensors were exposed to concentrations of $NO_2$ at 2, 5, 10, and 25 ppm. Data shown in FIG. 6 demonstrates that 5 ppm $NO_2$ converted to nitric acid (as a result of mixing with moist nitrogen) can elicit a phase transition in all 3 LCs deposited on the substrate. All concentrations of $NO_2$ tested in this study were detected by the LC sensors while exposure of the sensors to $N_2$ did not elicit a response (data not shown).

Example 4

Detection of a Derivative of Nitric Oxide Using LC-Based Sensors

This example describes the ability to convert nitric oxide to nitrogen dioxide by passing the former over a portion of potassium dichromate ($K_2Cr_2O_7$) oxidizing agent and to subsequently detect the derivative using LCs. The experiment was performed by using a single substrate that contained micropillar features. The substrate was treated with titanium and gold. The substrates were prepared by depositing ultrathin (optically transparent) gold films onto polymeric chips by electron beam deposition. Uniformly coated chips (100 Angstrom gold on a 15 Angstrom titanium adhesion layer) with micropillar features were spotted with <1 μl of the liquid crystal 5CB from a microcapillary pipette. The micropillars function to spread the LC by capillary action, support the thin film of LC, and dictate the thickness of the LC film based on the height of the pillars. A gas delivery system (as shown previously in FIG. 5) was used that allows dilution of an analyte to different known concentrations in the presence of humidity (~90-95% RH). Contents of certified gas cylinders of NO were diluted to known concentrations in a stream of humid nitrogen ($N_2$) using mass flow controllers. To generate $NO_2$ an oxidation tube containing $K_2Cr_2O_7$ was placed in-line and downstream of the NO source. The gas mixtures fed into an exposure chamber at a 100 sccm/minute rate and passed over the sensors for up to 15 minutes. The real-time appearance of the sensor was monitored by placing the exposure chamber, sandwiched by crossed polarizing filters, between a light box and a CCD based digital camera. Digital images of the sensor were collected every 30 seconds for the duration of exposure, converted to gray-scale intensity, and the luminosity quantified using ImageJ software from NIH.

Figure 7:
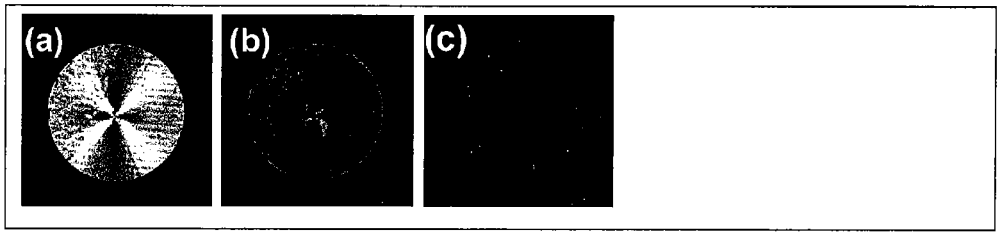
FIG. 7 is an image of optical appearance of a sensor viewed between crossed-polarizing filters (a) before, (b) during, and (c) at the end of 15 min exposure to a nitric oxide derivative. The active region on each sensor is 5 mm diameter.
Figure 8:
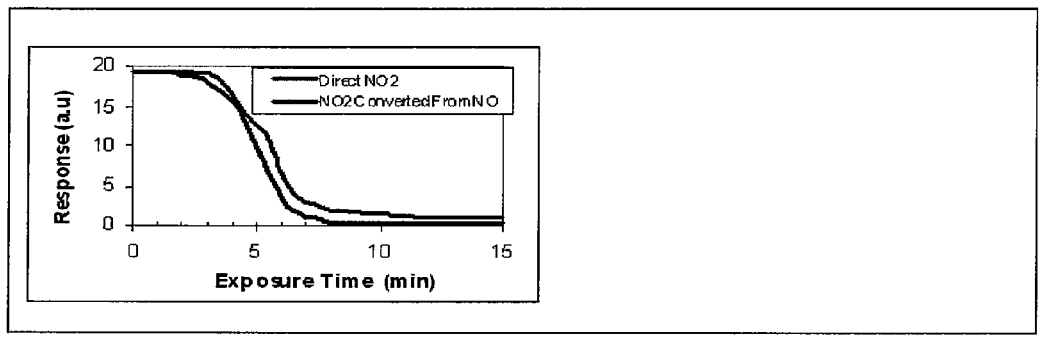
FIG. 8 is a graph of LC sensor responses to 5 ppm nitrogen dioxide from 2 sources. Nitrogen dioxide was diluted from a certified gas cylinder (i.e., direct NO2) and generated by conversion of nitric oxide.

Using the sensors, exposure system, and data acquisition method described above NO gas was delivered to the sensors but no measurable response was observed. After converting 5 ppm of NO to $NO_2$ in the presence of an oxidizer and humid $N_2$ a response was successfully elicited by the sensors as illustrated in FIG. 7. Initially the nematic LC is aligned in a random planar orientation on the substrate and initially appears bright when viewed between crossed polarizers as depicted in panel (a). Upon subsequent exposure to humid $NO_2$ the LC undergoes a phase transition from nematic to an isotropic liquid so that the sensor appears dark when viewed between crossed polarizers as shown in panel (c). The conversion of NO to $NO_2$ is simple and highly efficient. The responses of the sensors to humid $NO_2$ provided from a gas cylinder and generated by passing NO through the oxidizing agent were compared. FIG. 8 shows the kinetic profile of the sensor response to 5 ppm of $NO_2$ gas and to $NO_2$ converted from 5 ppm NO.

Example 5

Detection of Nitric Acid Vapor on LC Sensors Prepared with Glass Substrates

Figure 9:
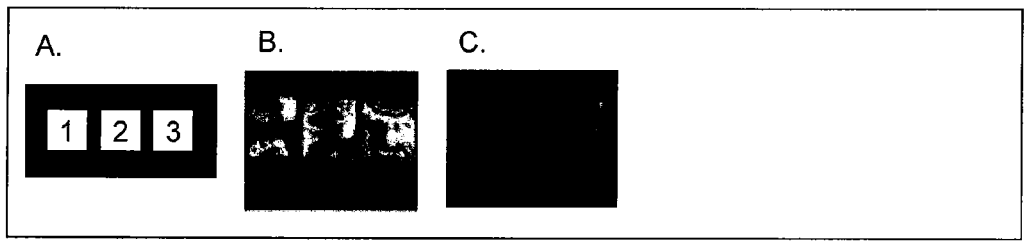
FIG. 9 provides a template and images of a sensor exposed to nitric acid vapor. The LCs were deposited in spots 1 (MLC 12200), 2 (MLC 6812), and 3 (5CB) on a cleaned glass slide. Images of the 1×3 sensor array are shown pre-exposure (B) and after 10 minutes of exposure to nitric acid vapors.

This example demonstrates the ability to detect analytes in vapor phase by use of LC sensors prepared on clean untreated, microscope slides from Fisher Scientific. Thin films of three different liquid crystals 5CB, MLC 6812, and MLC 12200 were prepared by depositing a small volume of LC onto glass substrates. The LC-coated substrates were placed in an exposure chamber along with another glass piece onto which 10 μl $HNO_3$ had been deposited. As the nitric acid vapor diffused through the chamber optical images of the LC-coated substrates were collected. FIG. 9 demonstrates that a phase transition of all three LCs was elicited on sensors fabricated on untreated glass slides in the presence of nitric acid vapor.

Example 6

Figure 10:
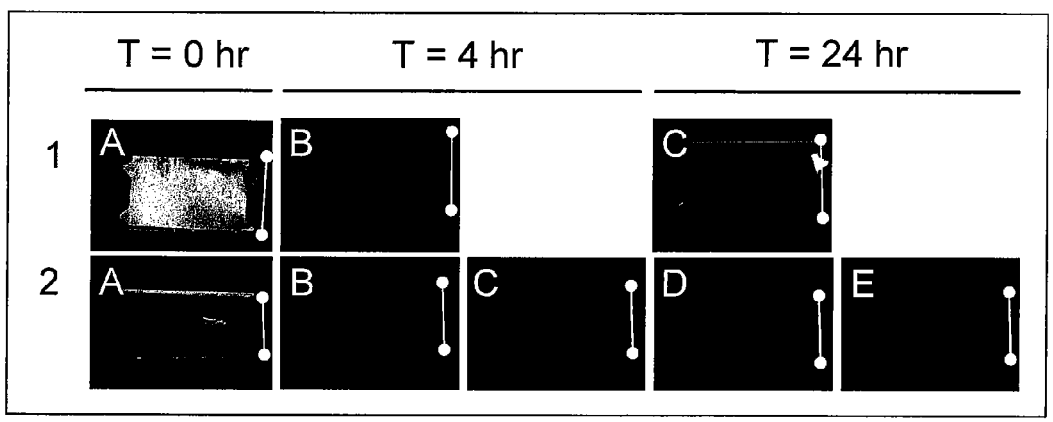
FIG. 10 provides representative images of the LC cells fabricated using OTS coated slides (1) and untreated glass slides (2) following 0, 4, and 24 hours of exposure to nearly saturated nitric acid vapor. In panels 2C and 2E the sensors were imaged at an inclined position with respect to the surface normal while all other images were captured while the sensors were in-plane. The white dumbbell shown in each panel indicates the outer edge of each sensor.

Detection of Nitric Acid Vapor on LC Sensors Prepared with OTS Treated Substrates In this example the LC sensors were in a "closed" cell format that was comprised of two surfaces. In one instance, the surfaces were glass slides that were cleaned but otherwise untreated. In another instance, the surfaces were cleaned and then coated with tridecafluoro-1,1,2,2-tetrahydrooctyl)triethoxysilane [OTS]. The OTS-coated surfaces were prepared on Lifter slips (Erie Scientific) that provided 25 um thick rails (i.e., spacers) on 2 opposing edges of the slide. OTS treatment on glass substrates was performed by 6 hour vacuum phase deposition. Next, the slides are ultrasonicated in ethanol for 10 minutes to remove the excess OTS and dried under a stream of nitrogen. In both sensor configurations the 2 surfaces were paired face to face and separated by a 25 μm gap. For untreated slides, thin mylar strips were applied to 2 sides of the slide sandwich to provide the 25 μm gap. The resulting cavity on each configuration was instilled with the LC 5CB. The closed LC cells were placed in an exposure chamber that was sandwiched between crossed polarizers. Nitric acid was added to the chamber and images of the cells were collected over a 24 hour period. In the sensor prepared with untreated glass surfaces the LC in nematic phase aligns in a random planar orientation and when viewed between crossed polarizers yields a bright appearance (see FIG. 10, panel 1A). After 4 hours of exposure to nitric acid vapor, the gas has begun to diffuse into the sensor through the gap provided by the spacer rails. The diffusion of $HNO_3$ into the LC leads to a transition from nematic phase to isotropic liquid. The change in phase of the LC gives rise to a visibly distinct band (see FIG. 10, panel 1B) that accompanies the time-dependent diffusion of the $HNO_3$ into the LC. The appearance of the band is caused by the change in optical properties of the LC accompanying the phase transition. Following a 24 hour exposure of the untreated glass LC sensor, the $HNO_3$ has diffused sufficiently far into the sensor to yield a fully dark appearance (FIG. 10, panel 1C) when placed between crossed polarizers. This dark appearance indicates that the film of nematic LC (formerly random planar in orientation) has transitioned to an isotropic liquid and no longer permits the passage of light when viewed between crossed polarizers. Also shown in FIG. 9 are images of the OTS-coated LC sensor. In this sensor, the LC aligns in a homeotropic orientation and that when viewed between crossed polarizers yields a dark appearance (see FIG. 10, panel 2A). After 4 hours of exposure to nitric acid vapor, the gas has begun to diffuse into the sensor through the gap provided by the mylar spacers. The diffusion of $HNO_3$ into the LC leads to a transition of the nematic LC to isotropic liquid. Nematic LC that is homeotropically oriented with respect to the surface and isotropic liquid will both yield a dark appearance when viewed between crossed polarizers making it difficult to discern any change in appearance of the LC (FIG. 7, panel 2B). Thus, the OTS-coated LC sensors rs were also imaged by tilting the exposure chamber at 40° with respect to the horizontal. In this inclined position it was possible to observe a wavefront moving from the edge of the sensor into the center. While the LC in the center of the sensor remains nematic and homeotropically aligned with respect to the surface it is no longer in-plane with respect to the light source and camera and yields a bright appearance. The change in phase of the LC on the edges gives rise to a visibly distinct band (see FIG. 10, panel 2C), due to diffusion of the HNO3 into the LC, and appearing dark when viewed between crossed polarizers irrespective of the inclined position of the sensor. Following a 24 hour exposure of the OTS-treated LC sensor to the HNO3 vapor, the band of isotropic liquid has increased in size but a portion in the interior of the LC cell remains homeotropic. This result was not visibly apparent when the cell was viewed in-plane but was observed by viewing the sensor at an incline (FIG. 10, panels 2D and 2E). The dark appearance at the perimeter of 2E indicates that the film of nematic LC (formerly homeotropic in orientation) has transitioned to an isotropic liquid (randomly orientated with respect to the surface) and no longer permits the passage of light when viewed between crossed polarizers.

Example 7

Figure 11:
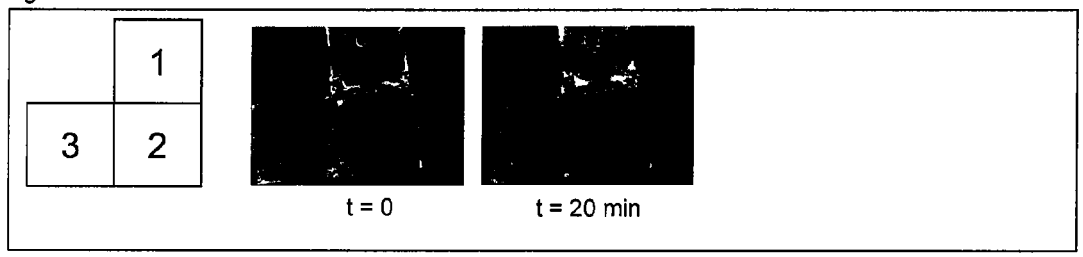
FIG. 11 provides images showing the effect of different surfaces on the response of LC Sensor to nitrogen dioxide exposure. Thin films of LC 5CB were prepared by spin coating a solution of 5CB in octane at 1:2 dilution on glass substrates which had been coated with (1) HMDS, (2) a gold layer, and (3) a gold layer treated with HMDS. Following exposure to 2 ppm of nitrogen dioxide vapor, the sensors prepared with gold and with HMDS on gold yielded a response. The sensor prepared with HMDS directly on glass did not yield a measurable response in the presence of nitrogen dioxide.

Effect of Different Surface Treatments on Sensor Response to Nitrogen Dioxide Exposure A feature of the LC sensors relies on the ability of the LC to wet the substrate surface and to maintain a uniform film thickness across the substrate. In this example, HMDS (1,1, 1,3,3,3-hexamethyldisilazane) was evaluated for its ability to assist with wetting the substrate and stabilizing the LC film. HDMS has been shown to improve the wetting property of substrates and has been widely used in photolithography to improve the adhesion of photoresist on glass substrate. Briefly, 1 cm×1 cm pieces of silicon and chips of gold-coated (20 A Ti underlying 100 A Au) served as the substrates. The substrates were cleaned by oxidation in a UV ozone cleaner for 10 minutes. One sensor comprised a cleaned silicon chip that was spin-coated with a layer of HDMS onto which 10 μl of a mixture containing equal parts of 5CB and octane was dispensed. A second sensor comprised a gold-coated chip onto which a 10 μl portion of the LC:octane mixture was dispensed. The final sensor comprised a gold-coated chip that was spin-coated with a layer of HDMS onto which a 10 μl portion of the LC:octane mixture was dispensed. The sensors were placed into an exposure chamber and exposed to 2 ppm of nitrogen dioxide for up to 20 minutes. The exposure chamber was sandwiched between crossed polarizers and images of the sensors were captured using a Basler digital camera (FIG. 11). demonstrates that all of the sensors initially appeared bright in the absence of nitrogen dioxide (t=0). However, following 20 minutes of exposure to NO2, sensor surfaces 2 and 3 appeared dark indicating a phase change from nematic liquid crystal to isotropic liquid. By contrast, the LC film on surface 1 (silicon treated with HDMS and LC) did not undergo a phase transition in the presence of $NO_2$. It is evident from the appearance of the film that the LC film supported on the glass substrate treated with HMDS is brighter than that on HMDS treated gold and bare gold. This indicates that the thickness of the film of LC on HMDS treated glass is greater than that on HMDS treated gold and bare gold.

Example 8

Use of Dopants in the LC Bulk to Shift the Nematic-Isotropic Transition Temperature It has been shown in the literature that arene-arene interactions between substituted aromatic solutes (dopants) and aromatic liquid crystal induce perturbations in the bulk properties of the liquid crystal phase. The introduction of a dopant in the LC host generally causes a shift in the nematic-isotropic transition temperature that is a function of dopant-host interactions. The purpose of this experiment was to dope two liquid crystals (5CB: 4'-Pentyl-4-biphenylcarbonitrile, and MLC12200-100) with known amounts of aromatic dopant (4-acetoxybiphenyl and 4-phenylpyridine) and examine their sensitivity towards detection of NO. The ultimate goal of this experiment was to identify the optimal concentration of dopant that will yield the greatest sensitivity of detection of NO through an optical change in the doped liquid crystal. To that end, each of the two aromatic compounds (4-acetoxybiphenyl and 4-phenylpyridine) were doped into the two LC candidates at 0.5, 2 and 4% mole:mole. The different mixtures at low to high dopant concentration were examined under microscope for their liquid crystalline phase. Finally, liquid crystals with and without dopants were exposed to a NO gas stream to examine the effect of the dopant on the sensitivity of the LC sensor to detect gas.

Figure 12:
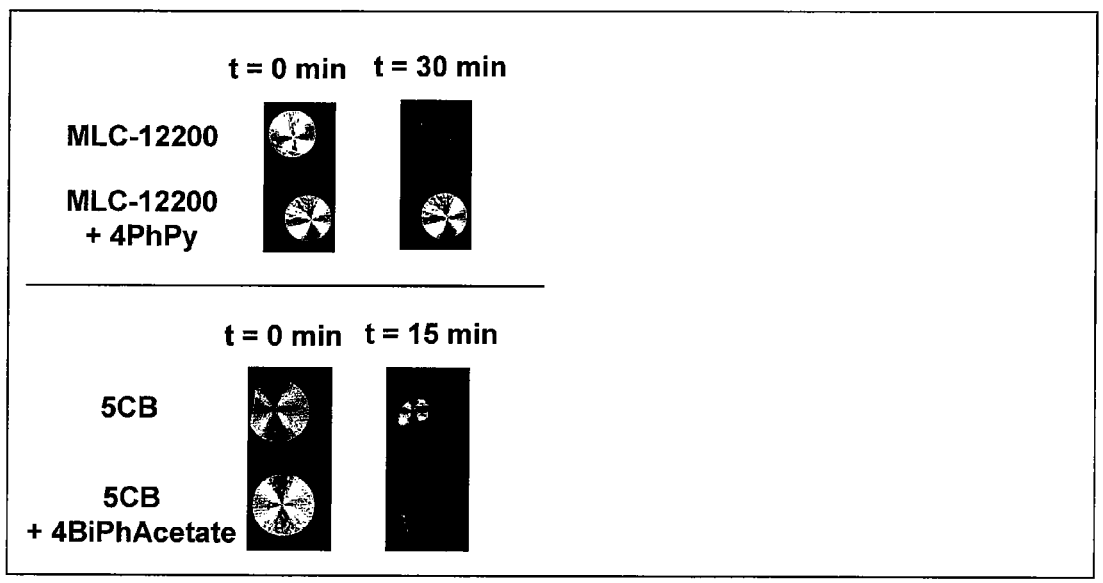
FIG. 12 provides images showing the effect of dopants on the response of LC sensors to NO gas. Sensors were prepared on micropillared substrates with LC alone or in combination with dopants and exposed to 10 ppm nitric oxide vapor for up to 30 minutes. Representative images of the sensors are shown pre and post-exposure.

Briefly, two hundred micro liters (200 μl) of LC were combined with 5-7 mg of solid dopant in a 0.5 ml centrifuge vial. The mixtures were placed in a 40° C. oven overnight to solubilize the dopant. The physical parameters were not known for all of the LCs, therefore calculations assumed that all LCs had a density of 1.0 and molecular weight of 250. In the first test, both liquid crystals were doped with either 4-Phenylpyridine (4PhPy) or 4-acetoxybiphenyl (4BiPhAcetate) at ~5% molar concentration. For all the liquid crystals tested, the addition of either doping agent reduced the N-I (nematic to isotropic) transition temperature. The phase transition temperature was qualitatively verified by using a slide warmer. Next, each LC solution (doped and undoped) was spotted on gold coated micropillared surfaces and tested for response to 10 ppm NO (by placing an oxidizer tube in line with nitrogen dioxide gas). The images are shown in FIG. 12. Sensors prepared with MLC-12200 alone responded more quickly to NO compared to those prepared with MLC-12200 and doped with 4PhPy (FIG. 12) or 4BiPhAcetate (data not shown). Sensors prepared with 5CB alone responded more slowly to NO compared to those prepared with 5CB and doped with 4PhPy (data not shown) or 4BiPhAcetate (FIG. 12).

Example 9

Contact Angle and LC Alignment

Figure 13:
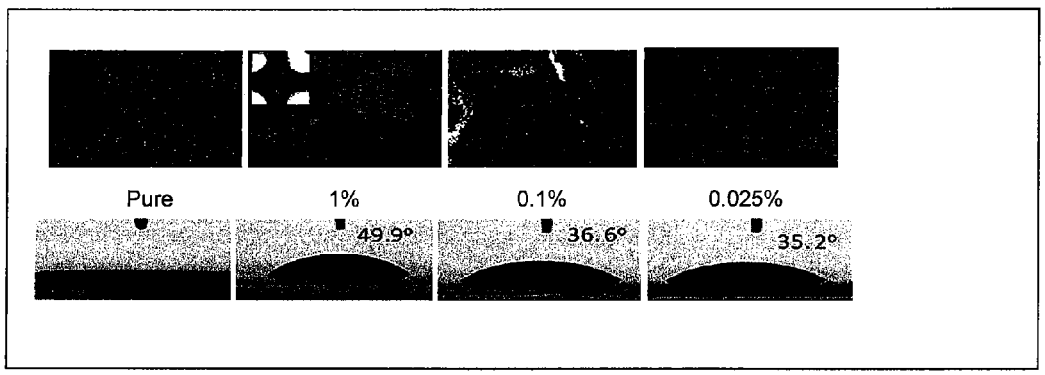
FIG. 13 provides images showing wetting and alignment behavior of $HNO_3$ doped E7 on UV ozone cleaned glass surfaces.

In this example, we measured the contact angle of LC deposited on cleaned glass surfaces. The surfaces were cleaned by UV ozone treatment for 3 minutes and then 10 μl droplets of E7 LC doped with varying concentrations of $HNO_3$ (ranging from 0.025% to 1%) were dispensed onto the surfaces. Contact angle measurements were assessed by use of a goniometer. Each surface was then paired with an OTS treated surface and LC was instilled into the 25 micron gap to form an LC cell. Cells were placed between crossed polarizers and viewed to determine orientation of the LC. The results indicate that there is a direct correlation between the contact angle of the LC mixture and the LC alignment on cleaned glass (FIG. 13). That is, a pure LC droplet wets the surface to yield a low contact (approaching 0°) and exhibits planar alignment with respect to the surface. A LC mixture containing 1% $HNO_3$ presents a contact angle of 49.9° and the LC appears homeotropic. In addition, the concentration at which homeotropic alignment is achieved depends on the surface used. For example, on the cleaned glass surface the LC transitioned from planar to homeotropic at a concentration greater than 0.1% but less than 1% $HNO_3$. However, on cleaned gold surfaces mixtures of LC doped with 0.1%, 0.25%, 1% and 5% $HNO_3$ all aligned homeotropic (data not shown) whereas pure LC aligned planar.

Figure 14:
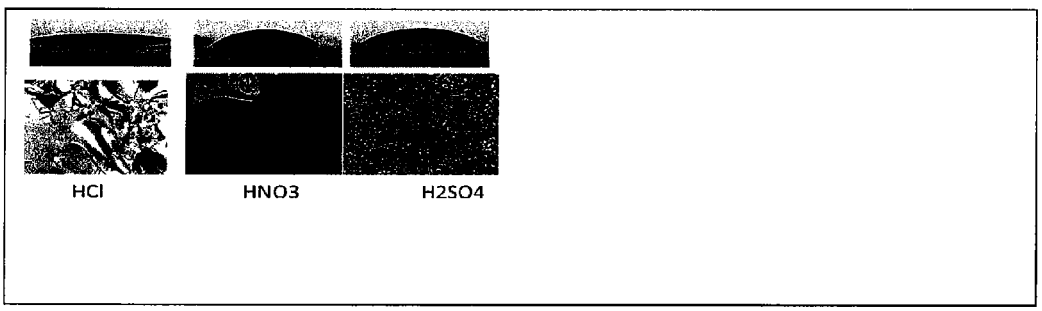
FIG. 14 shows wetting and alignment of 5CB doped with different acids (2%) on clean gold surfaces.

In follow-on studies, the LC 5CB was doped with 2% nitric acid, 2% sulfuric acid or 2% hydrochloric acid. The contact angles of these mixtures on freshly coated gold substrates were first measured and the same substrates were used to fabricate 25 μm cells with OTS secondary substrates. The results as shown in FIG. 14 indicate that the homeotropic alignment of 5CB occurs in the presence of nitric acid but not in the presence of other acids including HCl or $H_2SO_4$.

Figure 15:
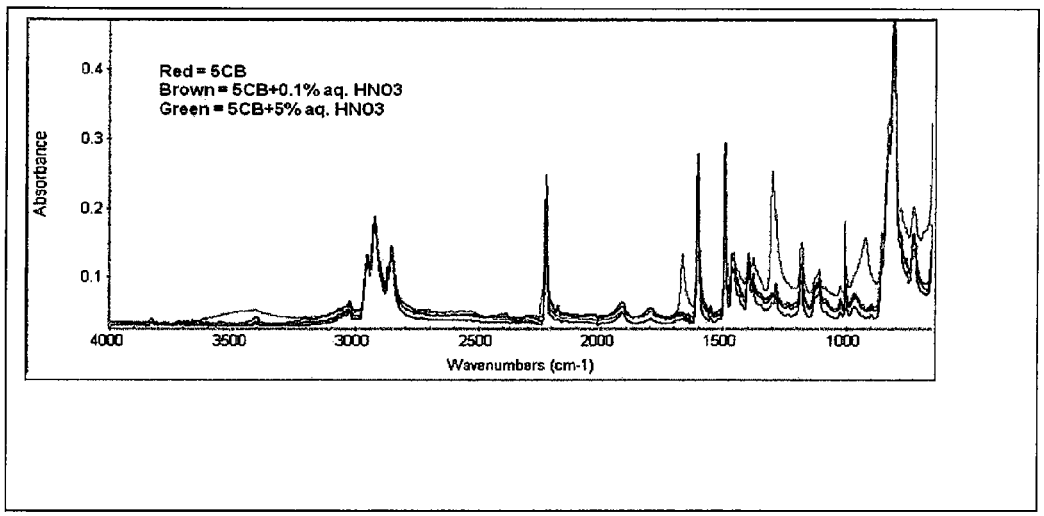
FIG. 15 provides the IR spectrum of 5CB doped with different concentrations of $HNO_3$. The spectra corresponding to 0.1% nitric acid doping is very similar to pure 5CB. The spectra corresponding to 5% nitric acid doping shows peaks corresponding to nitrates in nitric acid.

Pure 5CB and 5CB doped with 0.1% or 5% $HNO_3$ were subjected to Fourier Transform Infrared (FT-IR) spectroscopy studies. The FT-IR spectra suggests that there is not a measureable change in the spectra of 5CB compared to that of 5CB doped with $HNO_3$ concentrations below 0.1% (FIG. 15). When 5% $HNO_3$ was added to 5CB the FT-IR spectra indicates additional peaks representing the nitric acid but there is no obvious chemical change in the 5CB.

Example 10

In-Situ Exposure of LCs to $NO_2$

Figure 16:
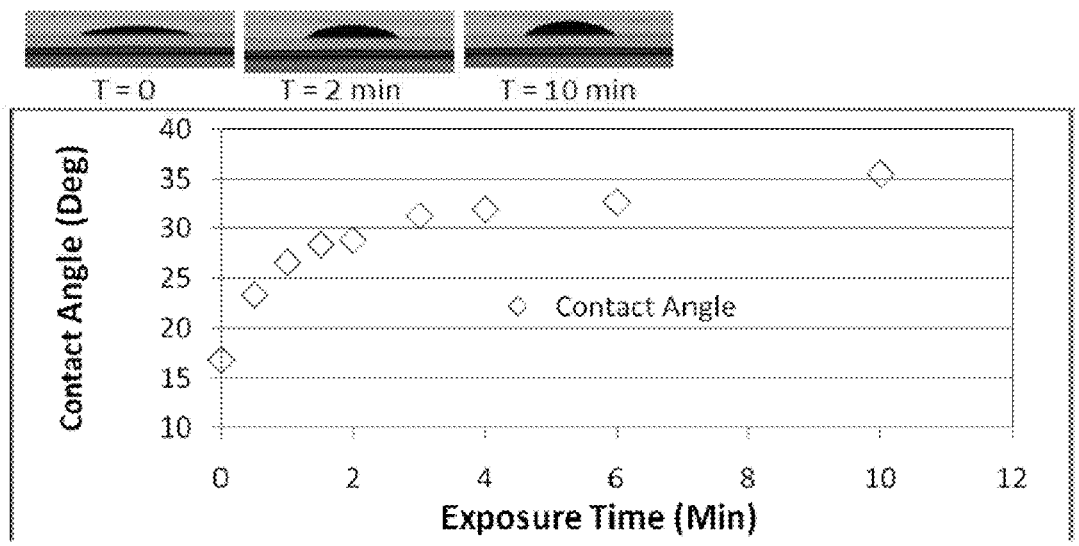
FIG. 16 shows the appearance of 5CB droplet and the correlation between the contact angle and exposure time as a thin film of 5CB is exposed to 500 PPM $NO_2$.

In this study, the exposure system was retrofitted to use a cuvette, commonly employed for UV-vis spectroscopy, as the exposure chamber. The cuvette was mounted onto the stage of a Goniometer and was modified to provide a small injection hole, for delivery of a precise volume of LC. In this manner, the LC droplet can be delivered directly to the test environment for contact angle measurement during $NO_2$ exposure. A gold coated substrate aged for one day in the lab environment was placed inside the cuvette and a cylinder with 500 PPM $NO_2$ was used to deliver gas to the test system. A 13 μl droplet of LC was dispensed onto the substrate, the digital images of the droplet were captured, and the contact angles were measured as a function of exposure time. The results in FIG. 16 show an increase in the contact angle of 5CB on the gold substrate as the length of exposure to $NO_2$ increases. Similar behavior was observed when a droplet of E7 was exposed to 500 PPM $NO_2$ (data not shown).

Example 11

$NO_2$ Bubbled Through 5CB

This experiment addresses whether changes in wetting properties of 5CB or E7 on gold surfaces upon exposure to $NO_2$ correlate with the LC alignment. A septum capped vial containing 0.5 ml 5CB was exposed to $NO_2$ by bubbling 500 PPM $NO_2$ into it for 30 mins at 50 sccm. The vial was then kept air tight and the LC was withdrawn using a Hamilton syringe. In a parallel manner, $N_2$ was bubbled at the same flow rate into another vial to serve as a control.

Figure 17:
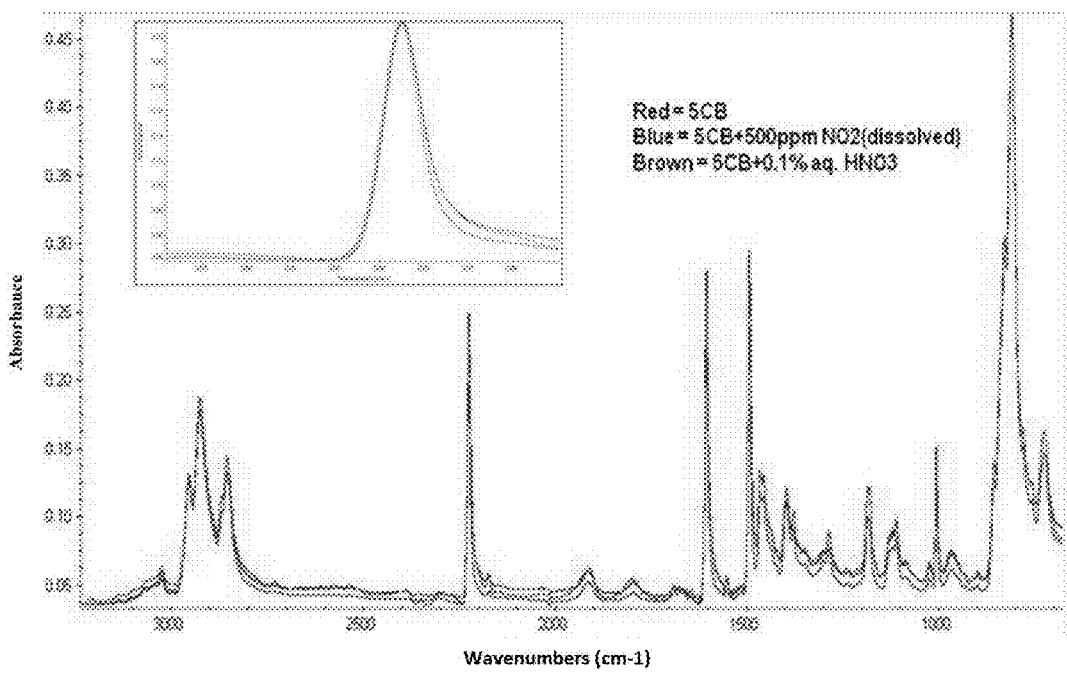
FIG. 17 provides the IR spectrum of 5CB exposed to $N_2$, $NO_2$ and doped with 0.1% HNO3 with an inset showing the CN stretch of 5CB.
Figure 18:
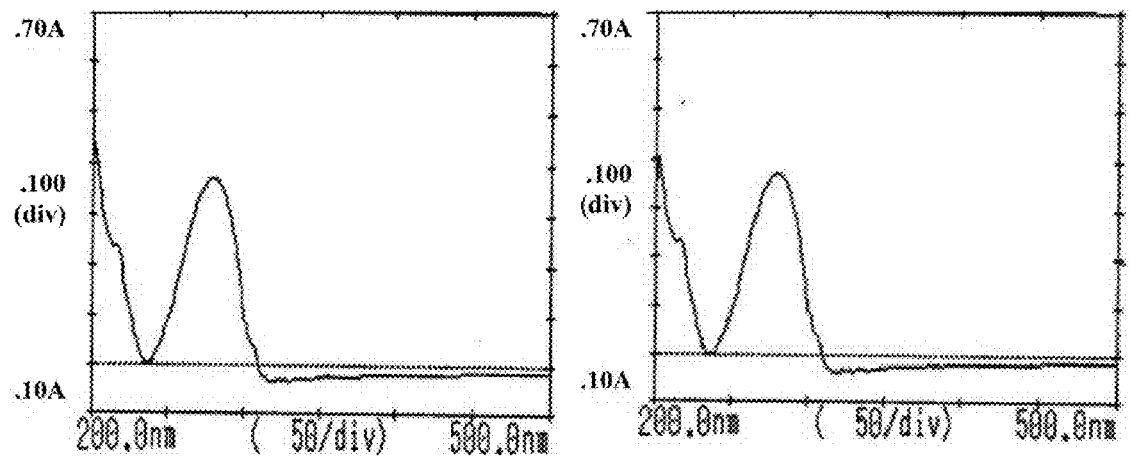
FIG. 18 provides UV vis spectroscopy of unexposed (left) and exposed 5CB.

These LC mixtures were first characterized by IR to assess any possible chemical changes. The results, as shown in FIG. 17, suggest that there are no significant chemical changes in 5CB that can be detected by IR. Next, when the 5CB that was exposed to $NO_2$ was subjected to UV vis spectroscopy, no shift in the peak absorption wavelength was observed that would indicate a change in the chemical structure of LC (FIG. 18).

Figure 19:
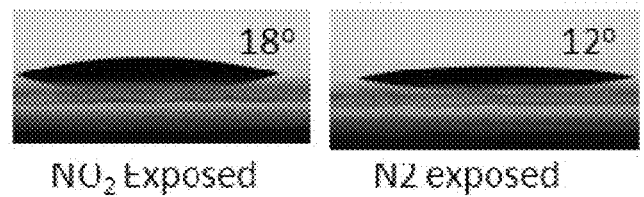
FIG. 19 shows that samples of 5CB pre-exposed to $NO_2$ and $N_2$ have different wetting properties when dispensed onto aged gold surfaces.
Figure 20:
FIG. 20 shows alignment of $NO_2$ exposed 5CB on fresh and $NO_2$ exposed gold surfaces.

These $NO_2$ exposed 5CB LC mixtures were deposited onto one-week aged gold surfaces and contact angles were measured. The 5CB exposed to $NO_2$ shows a greater contact angle than the 5CB exposed to $N_2$ (FIG. 19). The results suggest that there has been some change in the physical property of LC upon exposure to $NO_2$. The LC was next used to fabricate LC cells with surfaces that were either cleaned or pre-exposed to $NO_2$. The results, as shown in FIG. 20, demonstrate that pure (i.e., unexposed) LC aligns planarly when dispensed onto a cleaned gold surface and onto a gold surface that had previously been exposed to $NO_2$. When the LC is first exposed to $NO_2$ then dispensed onto the clean gold surface the LC prefers a homeotropic alignment. In contrast, when LC is exposed to $NO_2$ then dispensed onto a gold surface that has also been exposed to $NO_2$ the LC prefers a planar alignment.

Figure 21:
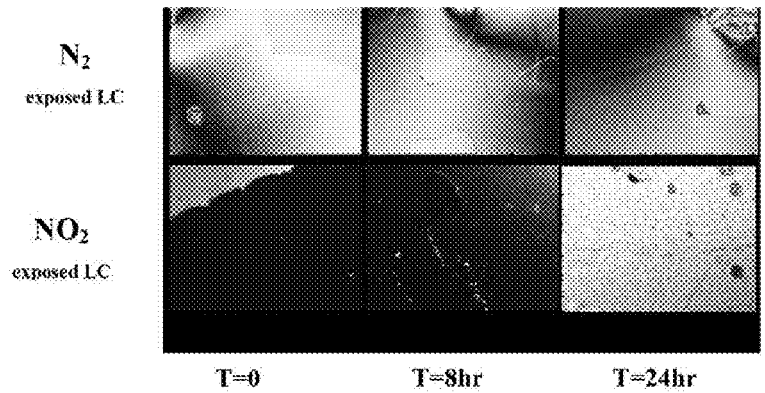
FIG. 21 shows alignment of $NO_2$ and $N_2$ Exposed 5CB dispensed onto ITO coated glass surfaces.

On the gold coated surfaces, 5CB, whether pure or exposed to $NO_2$ prefers to align homeotropic after some time. However, when pure and $NO_2$ exposed 5CB is dispensed onto indium tin oxide (ITO) coated surfaces the alignment of the LCs is distinct. FIG. 21 shows the optical images of the LC cells that were fabricated using ITO-treated glass slides. All slides were cleaned prior to use by ultrasonication in detergent, rinsing sequentially with acetone, IPA, and ethanol, and drying in a 100° C. oven. These cells were then filled with 5CB that had been previously exposed to $N_2$ or $NO_2$. The results, shown in FIG. 21, demonstrate that 5CB pre-exposed to $NO_2$ aligns LC homeotropically on the ITO coated surface whereas pure 5CB has been shown to exhibit planar alignment (not shown). However, this homeotropic alignment was lost by 24 hrs. Similar behavior has also been observed on freshly prepared gold surfaces. In contrast, 5CB pre-exposed to $N_2$ aligned planarly on the ITO surfaces and maintained that orientation for at least 24 hours. The results suggest that $NO_2$ dissolved in 5CB induces some change in the physical properties of LC that causes homeotropic alignment that manifests as difference in the anchoring property on the surface.

Example 12

Electrical Properties of Exposed 5CB

The following set of experiments was performed to test if there is a significant change in the electrical properties of LCs upon exposure to $NO_2$. Electrodes (5 mm×5 mm) that were 500 Angstrom thick were patterned on glass substrates. The electrodes were cleaned with acetone and ethanol then dried in an oven at 100° C. for 10 mins. Twenty five micron thick optical cells were fabricated with opposing electrodes facing each other. The capacitance and conductance of these empty cells were first measured using the Agilent LCR meter (E4980A) at different measurement voltage signals at 1 kHz. The cells were then carefully filled (without disturbing the setup to avoid any change in the stray capacitance) with $N_2$ exposed 5CB and $NO_2$ exposed 5CB and the capacitance and conductance were measured again. The ratio of the capacitance was calculated with LC versus with air between the electrodes to obtain the dielectric constant of the LC at different measurement voltages. The conductivity measurements were obtained with LC filling the gap. After the measurement was complete, an image of the LC cell was taken under a microscope to determine the orientation of LC inside the cell.

Figure 22:
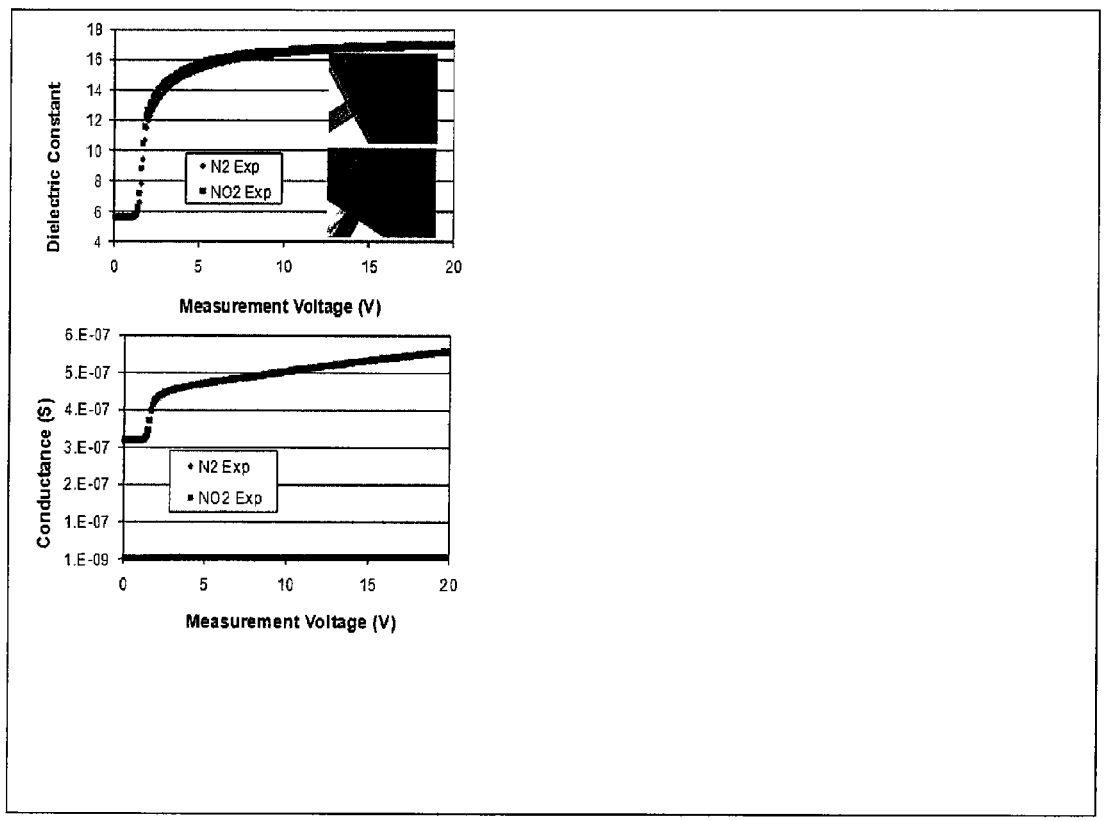
FIG. 22 shows samples of 5CB pre-exposed to $NO_2$ and $N_2$ have different wetting properties when dispensed onto aged gold surfaces.

The results as shown in FIG. 22 indicate that both $NO_2$ exposed LC and $N_2$ exposed LC exhibit planar alignment on these gold surfaces. As the measurement voltage increases the dielectric constant of the LC also increases which is consistent with the dielectric anisotropy of 5CB. There is no significant difference in the dielectric constant of $NO_2$ exposed LC and $N_2$ exposed LC except around the threshold voltage. It should be noted here that the threshold voltage depends on the spacing between two electrodes and there is probably a small difference in the thickness of the cells which may account for the small change in the dielectric constant. However, the $NO_2$ exposed LC has significantly higher (500×) conductivity compared to the $N_2$ exposed 5CB. Although the difference in the conductivity is significant, both of these LCs appear to align planar on the gold surfaces used in these experiments. This suggests that the differences in electrical conductance are not strictly a function of the orientation of the LC.

Example 13

LC Compositions with Reactive Moieties

Figure 23:
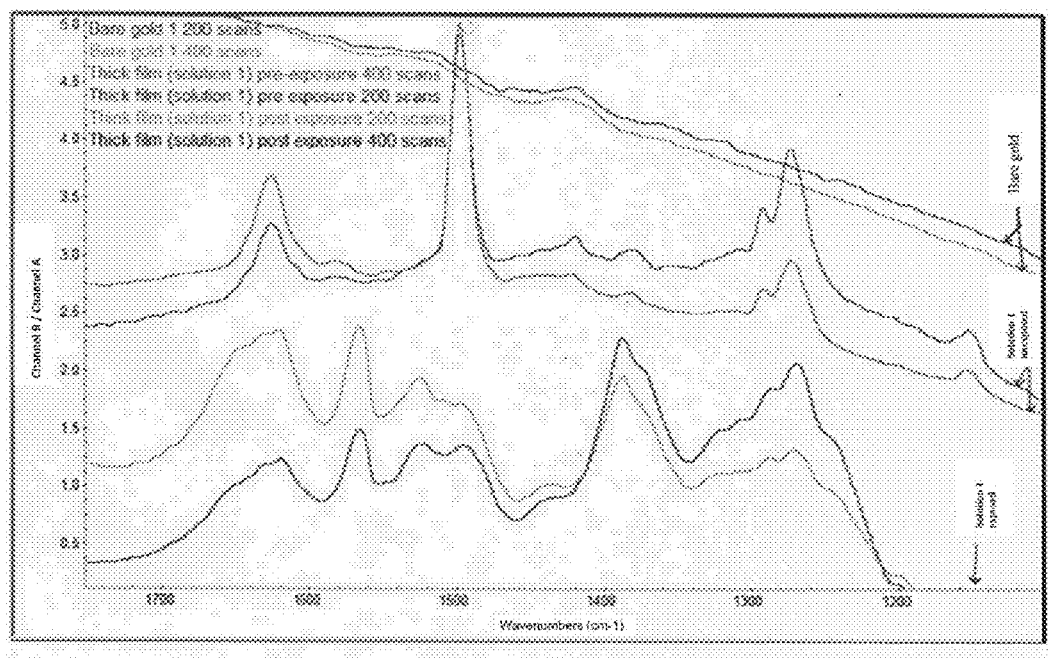
FIG. 23 shows changes in IR spectrum of 3,3'-Dimethylbenzidine following exposure to 10 PPM $NO_2$.

Gold coated glass pieces (1000 Å/50 Ti) were cut into several smaller pieces (18 mm×18 mm) and cleaned by washing with ethanol (10 sec) followed by drying with nitrogen (45 sec). Stock solutions of 3,3'-Dimethylbenzidine were prepared in ethanol solvent ranging 3 mM-30 mM in concentration. One hundred microliters of the respective solutions were dispensed onto clean gold coated glass slides and spin coated to get a dry uniform film. The thicknesses of the spin coated films were measured by ellipsometry to determine the consistency of the film. The solid 3,3'-Dimethylbenzidine formed a homogeneous film on the gold surface and its thickness correlated with the concentration of the stock solution used. A thirty millimolar solution (30 mM) resulted in the thickest film while the 3 mM solution resulted in the thinnest film. For exposure studies, 10 ppm of humid $NO_2$ was blown across the coated films for 10 minutes in a closed exposure chamber and the substrates were subjected to analysis by IR spectroscopy (FIG. 23). All of the films showed characteristic IR frequencies to confirm the reaction between 3,3'-Dimethylbenzidine and $NO_2$.

Similar reactions were observed with other substituted anilines including 4-aminothiophenol, 3,3',5,5'-Tetramethylbenzidine (data not shown). It is reasonable to expect that a change in the liquid crystal property will occur when any of these functionalities are incorporated in the liquid crystal.

Example 14

Detection by Changes in Capacitance

Figure 24:
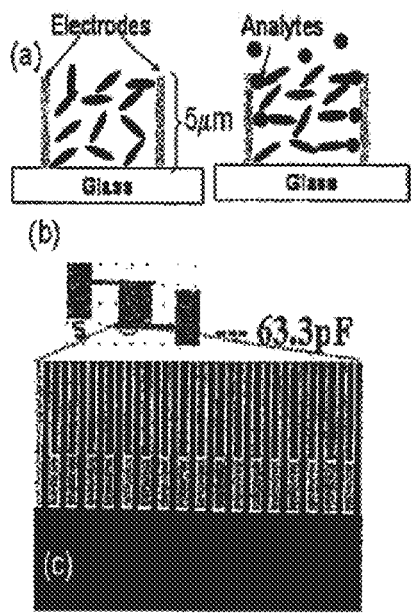
FIG. 24 shows: (a) Principle of analyte detection using capacitance measurement. A small change in the surface properties induces reorientation of LC that can be measured as a change in capacitance between thick electrodes. (b) Schematic of interdigitated electrodes used and (c) optical image of ~4 μm wide electrodes.

We evaluated the feasibility of detecting nitrogen dioxide ($NO_2$) by using capacitance measurements. A small change in the liquid crystal (LC) anchoring properties on a surface can be probed effectively using capacitance measurements by applying a high electric field during the measurement. Since the gas exposure system allows an uninterrupted measurement of capacitance, it has a potential to allow measurements of small changes in the surface properties without influenced by stray capacitance. The basic principle, electrode configuration and the optical image of the electrodes are shown in FIG. 24.

Figure 25:
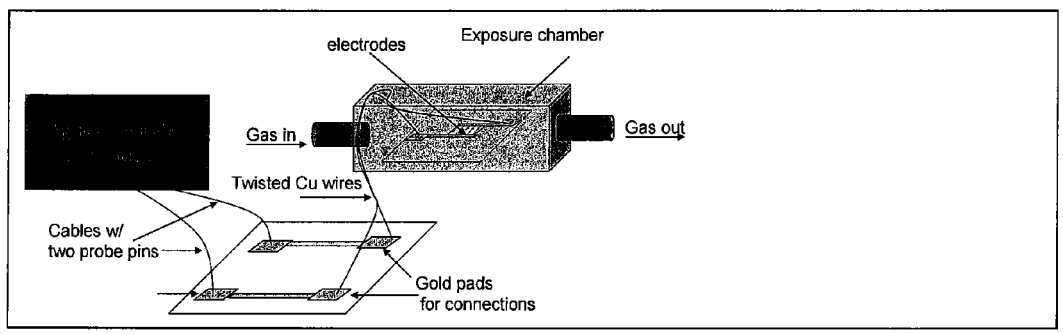
FIG. 25 provides a schematic of experimental setup for capacitance measurements (not to scale).

The capacitance of the interdigitated electrode was measured directly using an LCR meter. The electrodes as shown in FIG. 24 were UV ozone cleaned for 3-5 minutes and then placed on a hot plate at 50° C. to permit filling of sensors in isotropic phase. A small amount of the LC 5CB was applied to the center of the electrodes and allowed to spread to over the 4×4 mm area. The hot plate was then turned OFF to allow the LC to slowly cool to room temperature, excess LC was removed and the capacitance was measured at 100 mV (a voltage which does not have any significant effect on the orientation of LCs). Next, two pads of the electrodes were connected to 30 gauge twisted pair insulated copper wire as shown in FIG. 25. The remaining ends of the twisted wires were connected to a substrate with gold pads. The capacitance of the electrodes was then measured between the gold pads using two probe pins attached to the cables of the LCR meter. The stray capacitance introduced during these measurements comes from the twisted copper wires, as the effect of the cables up to the tip of the probe pins is compensated. The LC sensor with embedded electrodes was placed into an exposure chamber for testing. Typical capacitance values measured include: bare electrodes=61.27 pF, electrodes filled with LC=136 pF and between the gold pads including twisted wires=150.4 pF. The latter configuration indicates that approximately ~12 pF of additional capacitance is induced by the wires. For exposure, dry nitrogen dioxide was then introduced at flow rates of 100-500 sccm into the chamber.

Example 15

Detection by Changes in Capacitance

Figure 26:
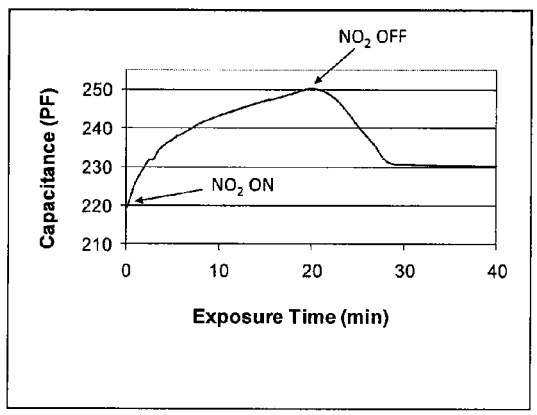
FIG. 26 shows capacitive response of the sensor to 50 ppm $NO_2$.

Using the interdigitated electrodes, exposure chamber, and measurement set up described previously in Example 16, the sensors were exposed to $NO_2$ and capacitance was measured. The new sensor was prepared by UV ozone cleaning for 5 minutes, filled with 5CB in isotropic phase and cooled to room temperature. The excess LC was wiped OFF and the sensor was set aside for 4 hrs for equilibration. The sensor was then placed in the exposure chamber and subjected to 50 ppm $NO_2$ at 200 sccm. Capacitance was measured as a function of exposure time at a measurement voltage of 1V. The capacitance measurement showed a measurable increase as a function of exposure time and there was no lag time between introduction of the gas and a change in capacitance (FIG. 26). After a 20 minute exposure, the $NO_2$ gas source was turned OFF and the sensor response was reversed. As indicated by the graph, the rise time of the sensor response differed from the fall time.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in organic chemistry, materials science, chemical engineering, or related fields are intended to be within the scope of the following claims.

What is claimed is:

1. A method of detecting a nitric oxide in a gaseous phase comprising:
   a) providing a liquid crystal assay device comprising at least one surface in contact with a liquid crystal composition comprising mesogens selected from the group consisting of MBBA, EBBA, MLC-6812, MLC 12200, 5CB (4-n-pentyl-4'-cyanobiphenyl), 8CB (4-cyano-4'octylbiphenyl) and 4-(trans-4-heptylcyclohexyl)-anilin;
   b) exposing said liquid crystal assay device to a sample suspected of containing nitric oxide; and
   c) interrogating said liquid crystal assay device to detect said nitric oxide, wherein a change in properties of the liquid crystal in said assay device caused by interaction of said nitric oxide with said liquid crystal composition is indicative of the presence of said nitric oxide.

2. The method of claim 1, wherein said interrogation step is performed by a method selected from the group consisting of measurement of change in optical anisotropy, magnetic anisotropy, dielectric anisotropy, and measurement of phase transition temperature.

3. The method of claim 1, wherein said interaction of said nitric oxide with said liquid crystal composition that is indicative of the presence of said nitric oxide is related to a pressure or temperature change in the presence of said nitric oxide.

4. The method of claim 1, wherein said liquid crystal assay device comprises an array of discrete assay areas and at least one internal calibration area and wherein said interrogation step further comprises comparing the differential response between said calibration area and at least one of said discrete assay areas.

5. The method of claim 1, wherein said surface is formed from a material selected from the group consisting of gold, glass and silicon.

6. The method of claim 1, wherein said surface has a form selected from the group consisting of planar, spherical and cylindrical.

7. The method of claim 1, wherein said surface is a patterned surface.

8. The method of claim 7, wherein said patterned surface comprises a feature selected from the group consisting of a grid, a channel, a plurality of channels, a plurality of pillars, or an array of assay areas or combination thereof.

9. The method of claim 8, wherein said features are 1 micron to 200 microns wide, 1 micron to 50 microns high and spaced 1 micron to 200 microns apart.

10. The method of claim 8, wherein said pillars comprise a shape selected from the group consisting of circular, triangular, square, hexagonal, or a combination thereof.

11. The method of claim 1, wherein said liquid crystal composition undergoes a phase transition in the presence of said nitric oxide from one phase selected from the group consisting of an isotropic phase, a nematic phase, and a smectic phase to another phase selected from the group consisting of an isotopic phase, a nematic phase and a smectic phase.

12. The method of claim 1, wherein said liquid crystal composition undergoes an orientational transition in the presence of said nitric oxide selected from the group consisting of homeotropic changing to a planar alignment, random planar alignment changing to uniform planar alignment, uniform planar alignment changing to random planar alignment, and planar alignment changing to homeotropic alignment.

13. The method of claim 1, wherein said liquid crystal composition comprises a dopant.

14. The method of claim 1 wherein said nitric oxide is a compound in breath.

15. The method of claim 1, wherein said gaseous phase is treated by an agent selected from the group consisting of oxidizing, reducing, and hydrating agents to provide a derivatized nitric oxide.

16. A method of assaying levels of exhaled nitric oxide comprising:
   a) providing a device comprising at least one surface in contact with a liquid crystal composition reactive with nitric oxide or a derivative thereof; and
   b) exposing said device to a breath sample suspected of containing nitric oxide, wherein presence of nitric oxide is indicated by a change in the properties of said liquid crystal composition.

17. The method of claim 16, wherein said exhaled nitric oxide is reacted with an oxidizing agent to provide nitric oxide derivatives; and exposing said device to said nitric oxide derivatives, wherein presence of nitric oxide is indicated by a change in the properties of said liquid crystal composition.

18. The method of claim 17, wherein the oxidized derivative is exposed to a humid atmosphere.

* * * * *